(12) United States Patent
Kirkland, III et al.

(10) Patent No.: US 8,821,884 B2
(45) Date of Patent: Sep. 2, 2014

(54) COMPOSITIONS AND METHODS USING MD-2 MUTANTS AND CHIMERIC PROTEINS

(75) Inventors: Theo N. Kirkland, III, La Jolla, CA (US); Sunganya Viriyakosol, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 943 days.

(21) Appl. No.: 11/572,799

(22) PCT Filed: Jul. 27, 2005

(86) PCT No.: PCT/US2005/026771
§ 371 (c)(1),
(2), (4) Date: Dec. 18, 2007

(87) PCT Pub. No.: WO2006/025995
PCT Pub. Date: Mar. 9, 2006

(65) Prior Publication Data
US 2008/0118504 A1 May 22, 2008

Related U.S. Application Data

(60) Provisional application No. 60/591,805, filed on Jul. 27, 2004, provisional application No. 60/681,097, filed on May 13, 2005.

(51) Int. Cl.
| | |
|---|---|
| *A61K 39/00* | (2006.01) |
| *A61K 39/38* | (2006.01) |
| *A61K 39/40* | (2006.01) |
| *A61K 39/385* | (2006.01) |
| *A61K 39/395* | (2006.01) |

(52) U.S. Cl.
USPC .............. 424/185.1; 424/130.1; 424/139.1; 424/150.1; 424/164.1; 424/178.1; 424/179.1; 424/180.1; 424/181.1; 424/182.1; 424/183.1; 424/184.1; 424/192.1; 424/193.1; 424/278.1; 424/400; 514/1.1; 514/1.3; 514/2.1; 514/21.2

(58) Field of Classification Search
None
See application file for complete search history.

(56) References Cited

U.S. PATENT DOCUMENTS

| 4,458,066 A | 7/1984 | Caruthers et al. |
| 4,683,195 A | 7/1987 | Mullis et al. |

(Continued)

FOREIGN PATENT DOCUMENTS

| WO | WO-96/39154 | 12/1996 | |
| WO | WO-97/03211 | 1/1997 | |
| WO | WO 01/90151 | * 11/2001 | ............. C07K 14/00 |

OTHER PUBLICATIONS

Kawasaki et al., (J. of Immunol. 2003. 170:413-420).*

(Continued)

*Primary Examiner* — Ja'Na Hines
(74) *Attorney, Agent, or Firm* — Gregory P. Einhorn; Gavrilovich, Dodd & Lindsey LLP

(57) ABSTRACT

The invention provides compositions and methods for the targeted bacteriostatic and antibacterial agents and for treatment of sepsis caused by infectious diseases, such as bacterial and fungal diseases. In one aspect, the invention provides methods and compositions for decreasing the levels of LPS in the circulation of an individual, e.g., a human patient with sepsis, e.g., gram negative septic shock. In one aspect, the invention is directed to chimeric proteins comprising the MD-2 polypeptide and an opsinizing agent, e.g., antibody Fc domains, or equivalent. In one aspect, the invention is directed to chimeric proteins comprising fragments or altered form of MD-2 polypeptide and an opsinizing agent, e.g., antibody Fc domains, or equivalent. The invention also provides pharmaceutical compositions comprising the chimeric polypeptides of the invention, and methods of making and using them, including methods for ameliorating or preventing sepsis. The invention also provides compositions for transfecting cells with nucleic acid comprising the mutant MD-2 proteins and/or the chimeric polypeptides of the invention.

22 Claims, 10 Drawing Sheets

(56) References Cited

U.S. PATENT DOCUMENTS

| | | | |
|---|---|---|---|
| 4,683,202 | A | 7/1987 | Mullis |
| 5,013,830 | A | 5/1991 | Ohtsuka et al. |
| 5,532,226 | A | 7/1996 | Demarest et al. |
| 5,684,148 | A | 11/1997 | Caruthers et al. |
| 5,716,928 | A | 2/1998 | Benet et al. |
| 5,721,118 | A | 2/1998 | Scheffler |
| 5,858,401 | A | 1/1999 | Bhalani et al. |
| 5,962,674 | A | 10/1999 | Iyer et al. |
| 6,001,982 | A | 12/1999 | Ravikumar et al. |
| 6,007,839 | A | 12/1999 | Mayhew et al. |
| 6,025,155 | A | 2/2000 | Hadlaczky et al. |
| 6,031,092 | A | 2/2000 | Just et al. |
| 6,063,400 | A | 5/2000 | Geho et al. |
| 2002/0107201 | A1 | 8/2002 | Arana Rosainz et al. |
| 2003/0108573 | A1 | 6/2003 | Proppert |
| 2003/0232352 | A1 | 12/2003 | Schwartz et al. |
| 2004/0028670 | A1 | 2/2004 | Carlson et al. |
| 2004/0038288 | A1 | 2/2004 | Huang et al. |
| 2004/0137001 | A1 | 7/2004 | Schreiber et al. |
| 2004/0235195 | A1 | 11/2004 | Wada et al. |
| 2005/0037964 | A1 | 2/2005 | Griffin et al. |
| 2005/0048655 | A1 | 3/2005 | Novitsky et al. |
| 2005/0069972 | A1 | 3/2005 | Castro et al. |

OTHER PUBLICATIONS

Viriyakosol et al., (J. Biol. Chem. 2001. vol. 276(12):38044-38051).*
Adams et al., J. Am. Chem. Soc. (1983) 105:661-663.
Akashi et al., J. Exp. Med. (2003) 198:1035-1042.
Akashi et al., J. Immunol. (2000) 164:3471-3475.
Al-Muhammed et al., J. Microencapsul. (1996) 13:293-306.
Altwegg and Kubli, Nucleic Acids Res. Symp. Ser. (1980) 215-223.
Barringer et al., Gene (1990) 89:117-122.
Beaucage, Tetra. Lett. (1981) 22:1859.
Belousov et al., Nucleic Acids Res. (1997) 25:3440-3444.
Blommers et al., Biochemistry (1994) 33:7886-7896.
Brophy et al., Eur. J. Clin. Pharmacol. (1983) 24:103-108.
Brown et al., Meth. Enzymol. (1979) 68:109-151.
Burg et al., Mol. Cell. Probes (1996) 10:257-271.
Caruthers et al., Cold Spring Harbor Symp. Quant. Biol. (1982) 47:411-418.
Chonn and Cullis, Curr Opin. Biotechnol. (1995) 6:698-708.
Da Silva Correia et al., J. Biol. Chem. (2001) 276:21129-21135.
Da Silva Correia and Ulevitch, J. Biol. Chem. (2002) 277:1845-1854.
Delude et al., J. Immunol. (1998) 161:3001-3009.
Eyles et al., J. Pharm. Pharmacol. (1997) 49:669-674.
Fotherby, Contraception (1996) 54:59-69.
Frenkel et al., Free Radic. Biol. Med. (1995) 19:373-380.
Gao et al., Pharm. Res. (1995) 12:857-863.
Genbank Accession No. AB018549.
Geysen et al., Proc. Natl. Acad. Sci. USA (1984) 81:3998-4002.
Gioannini et al., Proc. Natl. Acad. Sci. USA (2004) 101:4186-4191.
Groning, Pharmazie (1996) 51:337-341.
Guatelli et al., Proc. Natl. Acad. Sci. USA (1990) 87:1874-1878.
Hidalgo-Aragones et al., J. Steroid Biochem. Mol. Biol. (1996) 58:611-617.
Horn et al., Nucleic Acids Res. Symp. Ser. (1980) 225-232.
International Search Report for PCT/US05/26771, date mailed on Apr. 10, 2007, 4 pages.
Johnson et al., J. Pharm. Sci. (1995) 84:1144-1146.
Johnson, ed., Posttranslational Covalent Modification of Proteins, Academic Press, New York, 1983, pp. 1-12.
Kawasaki et al., J. Immunol. (2003) 170:413-420.
Kern and Hampton, Biotechniques (1997) 23:120-124.
Kimmel and Berger, Methods Enzymol. (1987) 152:307-316.
Kwoh et al., Proc. Natl. Acad. Sci. USA (1989) 86:1173-1177.
Landegren et al., Science (1988) 241:1077-1080.
Mancek et al., Biochem and Biophy Res. Commun. (2002) 292:880-885.
Mata, Toxicol. Appl. Pharmacol. (1997) 144:189-197.
Merrifield, J. Am. Chem. Soc. (1963) 85:2149-2154.
Merrifield, Methods Enzymol. (1997) 289:3-13.
Milligan et al., J. Med. Chem. (1993) 36:1923-1937.
Minto et al., J. Pharmacol. Exp. Ther. (1997) 281:93-102.
Miyake et al., J. Endotoxin Res. (2000) 6(5):389-391.
Mullen et al., Proc. Natl. Acad. Sci. USA (2003) 100:3919-3924.
Narang et al., Meth. Enzymol. (1979) 68:90-98.
Ohnishi et al., J. Immunol. (2001) 167:3354-3359.
Ostro, Am. J. Hosp. Pharm. (1989) 46:1576-1587.
Randow and Seed, Nat. Cell. Biol. (2001) 3:891-896.
Rao, J. Biomater Sci. Polym. Ed. (1995) 7:623-645.
Re and Strominger, J. Biol. Chem. (2002) 277:23427-23432.
Re and Strominger, J. of Immun. (2003) 171:5272-5276.
Roberge et al., Science (1995) 269:202-204.
Rohatagi et al., J. Clin. Pharmacol. (1995) 35:1187-1193.
Rohatagi, Pharmazie (1995) 50:610-613.
Rosenfeld, Nat. Genet. (1997) 15:333-335.
Samstag et al., Antisense Nucleic Acid Drug Dev (1996) 6:153-156.
Schromm et al., J. Exp. Med. (2001) 194(1):79-88.
Shimazu et al., J. Exp. Med. (1999) 189(11):1777-1782.
Smith et al., J. Clin. Microbiol. (1997) 35:1477-1491.
Sooknanan and Malek, Biotechnology (1995) 13:563-564.
Spatola, Chemistry and Biochemistry of Aminco Acids, Petides and Proteins (1983) 7:267-357.
Stewart et al., Solid Phase Peptide Synthesis, 2nd ed., Pierce Chemical Co., Rockford, Ill, 1984, pp. 11-12.
Strauss-Soukup et al., Biochemistry (1997) 36:8692-8698.
Tjwa, Ann. Allergy Asthma Immunol. (1995) 75:107-111.
Viriyakosol and Kirkland, J. Biol. Chem. (1995) 270:361-368.
Viriyakosol et al., J. Biol. Chem. (2000) 275:3144-3149.
Viriyakosol et al., J. Biol. Chem. (2001) 276:38044-38051.
Visintin et al., J. Biol. Chem. (2003) 278:48313-48320.
Visintin et al., Proc. Natl. Acad. Sci. USA (2001) 98(21):12156-12161.
Ward et al., Nature (1989) 341:544-546.
Wilson et al., J. Immunol. Methods (1994) 175:267-273.
Woon et al., Genomics (1998) 50:306-316.
Wu and Wallace, Genomics (1989) 4:560-569.
Yarmush et al., J. Biochem. Biophys. Methods (1992) 25:85-97.

* cited by examiner

Figure 4

```
            aaaa    aaaaa      AAAAA
  AAAAA           AAAAA       AAAAA      AAAAA
EAQKQYWVCNSSDASISYTYCDKMQYPISINVNP
                           aaaaa
     aaaaa       aaaaa aaaaa       aaaaa    aaaaa
  aaaaa           AAAAA       AAAAA     AAAAA        AAAAA
CIELKGSKGLLHIFYIPRRDLKQLYFNLYITVNTMNLPKRKEVICRGSDDDYSF
              aaaaa                                a Membrane MD-2

Soluble MD-2

Figures 9A *and* 9B
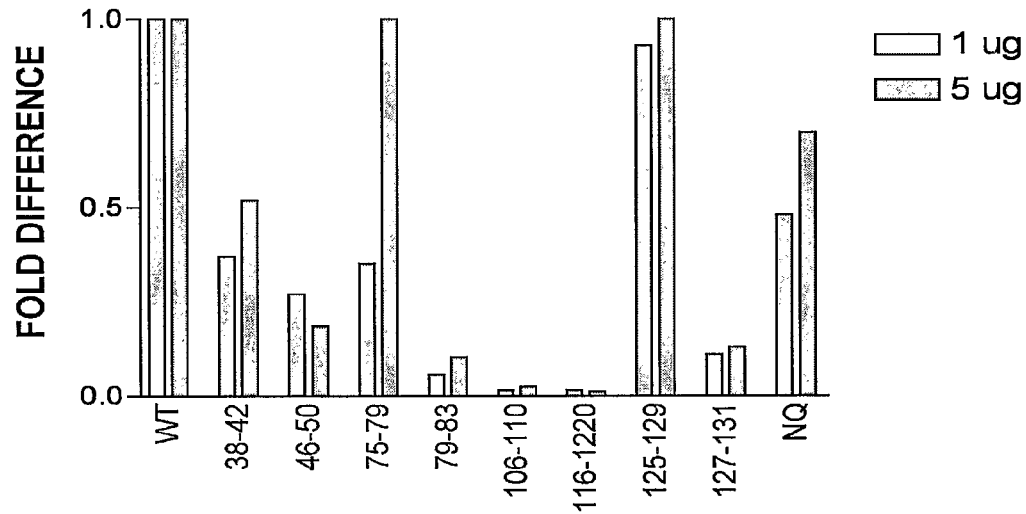
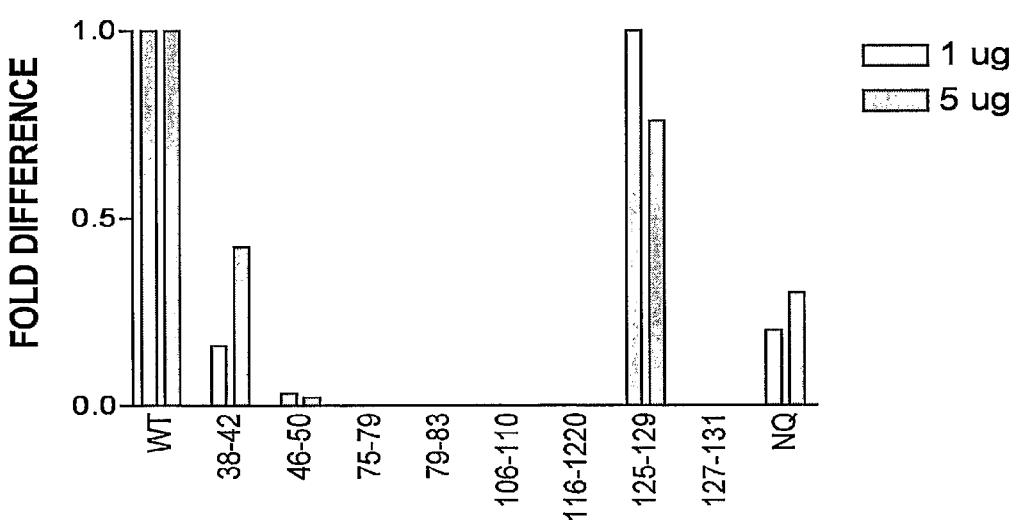

… # COMPOSITIONS AND METHODS USING MD-2 MUTANTS AND CHIMERIC PROTEINS

FEDERAL FUNDING

This invention was produced in part using funds from the Federal government under NIH Grant Nos. PO1GM37696 and GM066119. Accordingly, the Federal government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 220002066700Seqlist.txt | Nov. 30, 2007 | 50,708 bytes |

TECHNICAL FIELD

This invention relates to microbiology and infectious diseases, molecular and cellular biology and biochemistry. In one aspect, the invention is directed to the treatment of sepsis caused by infectious diseases, such as bacterial and fungal diseases. In one aspect, the invention provides variant MD-2 polypeptides and methods of using them, e.g., as bacteria-targeting agents, including use as antibacterial agents and to treat sepsis. In one aspect, the invention is directed to chimeric proteins comprising these mutant MD-2 polypeptides and an opsinizing agent, e.g., antibody Fc domains, or equivalent. In one aspect, these chimeric proteins are used as bacteria-targeting agents to deliver compositions, including other protein moieties. In one aspect, these chimeric proteins are used to treat sepsis or any gram-negative bacterial infection. In one aspect, the invention is directed to chimeric proteins comprising fragments or altered or truncated forms of MD-2 polypeptide and an opsinizing agent, e.g., antibody Fc domains, or equivalent. In other aspects the mutant MD-2 protein is joined or fused to a bacteriocidal moiety (e.g., a bacteriocidal protein domain) or to an antibiotic. The invention also provides pharmaceutical compositions comprising the chimeric polypeptides of the invention, and methods of making and using them, including methods for ameliorating or preventing sepsis. The invention also provides compositions for transfecting cells with nucleic acid comprising the mutant MD-2 proteins and/or the chimeric polypeptides of the invention.

BACKGROUND

Serious bacterial infections are a common cause of morbidity and mortality in the U.S. and around the world. The development of relatively antibiotic resistant bacteria has made this problem more difficult to treat with antibiotics.

In the past, antibody therapy has been used successfully to treat bacterial infections. *Pneumococcal pneumonia* and *pneumococcal* sepsis responded to treatment with antibody to *pneumococcal polysaccharide* in the pre-antibiotic era. However, the development of highly effective antibiotics for bacterial infections made this approach obsolete. There were also problems with antibody therapy. Each type of *pneumococcal* capsule required a specific antiserum, making therapy expensive and cumbersome. In addition, because the antisera were made in horses, toxic immunologic reactions (serum sickness) were a serious side effect. Furthermore, antibody therapy had no effect against other pathogens, such as *Staphylococcus* or gram-negative bacteria, because of the specificity of the antisera for the *pneumoccocal* polysaccharide.

The development of antibiotic resistance by bacterial has seriously altered our ability to combat bacterial infections with antibiotics. The development of vancomycin-resistant enterococci, methicillin-resistant *Staphylococcus*, and multi-drug resistant Gram-negative bacteria has limited the number of effective antibiotics. Though the search for new antibiotics has intensified, additional therapeutic approaches are needed.

Innate immunity is the first line of defense against pathogens. A key component of the mammalian innate immune system is a family of toll like receptors (TLRs). Lipopolysaccharide (LPS), a major component of gram-negative bacteria, activates a variety of cells to produce inflammatory cytokines leading to septic shock in humans. The innate immune mechanism that recognizes LPS involves a transfer of LPS to a pattern recognition molecule CD14 by LBP. Toll like receptor 4 (TLR4) is a type 1 transmembrane protein that has extracellular leucine rich repeats and an intracellular signaling domain that is responsible for LPS signaling. TLR4 is complexed with MD-2, a 22-25 Kd glycoprotein, on the cell surface. A cascade of events leading to maximal cellular activation is likely to involve transferring of LPS by LBP to CD14 and then to TLR4/MD-2. Although CD14 and LBP enhance cellular activation, activation of TLR4 by LPS absolutely requires MD-2.

MD2 is a pattern recognition receptor that binds LPS with a high affinity (an apparent Kd of 65 nM) and without the need for LPS binding protein to catalyze the reaction. It is an extracellular protein that is co-expressed with TLR4, and necessary for TLR4 LPS receptor function. Truncation of MD2 leads to LPS non-responsiveness and a monoclonal antibody that recognizes the MD2/TLR4 complex blocks LPS activation of cells.

MD-2 can be found on the cell surface in association with TLR4 or as a secreted protein. It shares a sequence homology to MD-1, a protein that binds to another TLR family member, RP105, that constitutes an LPS signaling complex on B-cells. MD-2 contributes to ligand recognition of TLR4. It binds LPS with high affinity and discriminates ligand recognition between mouse and human TLR4 to Taxol and lipid IVa. Interaction of cell surface TLR4/MD-2 complex by LPS-induced clustering of TLR4 leads to signal cellular activation.

Although proper glycosylation and trafficking TLR4 to the cell surface requires intracellular association with MD-2, functional TLR4 can be presented on the cell surface without MD-2 in both transfected cells and human airway epithelial cells. These cells can respond to LPS only in the presence of soluble MD-2. While soluble MD-2 (sMD-2) is essential for LPS induced activation of cells expressing only TLR4, high levels of sMD-2 inhibit cellular response to LPS in a whole blood assay or activation of U373 cells, presumably by sequestering LPS. Soluble MD-2 exists as the heterogeneous collection of monomer and oligomers through inter and intra chain disulfide bonds. It has been unclear how the different isoforms function.

Human MD-2 contains 160 amino acids residues, including the N-terminal 17 amino acid signal sequence, with 7 cysteine residues and 2 N-glycosylation sites.

SUMMARY

The invention provides compositions and methods that act as targeting agents for microorganisms, e.g., LPS-comprising microorganisms. In one aspect, the invention provides targeted antibacterial agents and for treating sepsis, e.g., due to Gram-negative and Gram positive bacteria. In one aspect, the compositions of the invention comprise variant MD-2 proteins, e.g., human MD-2, including truncation and sequence variant forms of MD-2. In one aspect, the compositions of the invention comprise chimeric molecules comprising the truncation and sequence variant forms of MD-2 of the invention and another molecule, such as an antibiotic, protein binding site (e.g., antibody Ag binding fragment or Fc fragment), protein ligand, activated protein C, cytokine, a small molecule, or a combination thereof. Thus, in alternative aspects the compositions of the invention can be used to activate complement, as opsinizing agents, as bacteriostatic or antibacterial agents, with therapy with activated protein C (e.g., recombinant human activated protein C (drotrecogin alfa, XIGRIS™) for, e.g., ameliorating sepsis-induced disseminated intravascular coagulation), to neutralize or compartmentalize lipopolysaccharide (LPS) and/or to ameliorate or treat septic shock.

The invention provides engineered polyspecific antibody-like proteins that bind to a variety of bacterial and fungal products, thereby opsonizing them for complement fixation and phagocytosis. In one aspect, the invention provides engineered MD-2 chimeric molecules (including recombinant fusions) comprising antibiotics, e.g., antibiotic peptides or proteins, that can target one or more antibiotics to a bacterial surface. The chimeric molecules of the invention can be designed to bind to a variety of bacterial and fungal products, thereby in one aspect facilitating opsonization for complement fixation and/or phagocytosis. Thus, in one aspect, the compositions and methods of the invention can be used to treat or prevent a wide variety of infections (e.g., bacterial or fungal) or the symptoms they cause. In an alternative aspect, the compositions and methods of the invention can provide a useful adjunct to antibiotic therapy for a wide variety of infections (e.g., bacterial and fungal infections) e.g., therapy with activated Protein C, or as an adjunctive treatment, e.g., with chemotherapy or transplant-related immune suppression treatment.

In one aspect, where the mutant MD-2 of the invention is joined (e.g., fused, as in recombinantly fused) to an Fc domain, the chimeric protein might function in several ways in the body (where the invention is not limited by any particular mechanism of action). For example, in one aspect, the chimeric proteins of the invention act to enhance clearance of bacterial endotoxin or to neutralize bacterial endotoxin. In one aspect, the chimeric proteins of the invention act to enhance opsonization of Gram-negative bacteria. In one aspect, the chimeric proteins of the invention act to enhance or initiate complement-mediated killing of Gram-negative bacteria.

As MD-2 binds lipopolysaccharide (LPS), a chimeric molecule of the invention (having at least two domains) comprising MD-2 comprising an LPS binding domain with at least a second domain—where the MD-2 comprising an LPS binding domain is used to target and/or deliver any moiety to an LPS-comprising bacterial surface, including targeting or delivering an opsinizing agent (e.g., an Fc domain), a protein C (e.g., a human activated protein C), an antibacterial or bacteriostatic peptide or protein, an antibiotic, a cytokine, an immunoregulatory agent, an anti-inflammatory agent, a complement activating agent, such as a collagen-like domain or a fibrinogen-like domain (e.g., a ficolin), carbohydrate-binding domains, and the like and combinations thereof, to a bacterial or any other LPS-comprising surface (e.g., a contaminated surface).

In one aspect, where the mutant MD-2 of the invention is joined (e.g., fused, as in recombinantly fused) to an anti-infectious agent, e.g., a bacteriostatic or an antibacterial (such as an antibacterial peptide domain), the chimeric protein the fusion protein functions as a targeted antibacterial agent. In one aspect, the fusion proteins are engineered as bivalent dimers comprising a mutant MD2-Fc fusion protein and a mutant MD2-antibacterial peptide fusion protein.

The invention provides chimeric proteins comprising a first domain comprising an MD-2 polypeptide (e.g., a mutant or truncated MD-2 of the invention) and a second domain comprising an opsinizing agent. In one aspect, the opsinizing agent comprises an antibody Fc domain, or Fc receptor-binding fragment thereof. In one aspect, the opsinizing agent or the MD-2 polypeptide comprises a human opsinizing agent or the MD-2 polypeptide.

MD-2 peptides or polypeptides used in the compositions (including pharmaceutical formulations) and methods of the invention can comprise a variant (e.g., a mutant sequence, or a truncation, or both), including variants of the human MD-2 polypeptide, e.g., as described herein, or, e.g., by Re (2003) J. Immunol. 171(10):5272-5276. The MD-2 variant can bind lipopolysaccharide (LPS) but not TLR-4, e.g., as the exemplary MD-2 variants of the invention having a sequence as set forth in SEQ ID NO:37, SEQ ID NO:38, SEQ ID NO:39. The MD-2 variant can have increased affinity for LPS. The MD-2 variant can have increased affinity for toll like receptor 4 (TLR4) or CD14 or LPS or a combination thereof. The MD-2 polypeptide can comprise a truncation of a human MD-2 polypeptide, e.g., as described herein, or, e.g., by Re (2003) J. Immunol. 171(10):5272-5276. In one aspect, the truncated MD-2 has increased affinity for LPS. The truncated MD-2 can have increased affinity for toll like receptor 4 (TLR4) or CD14 or LPS or a combination thereof.

In one aspect, the MD-2 comprises the naturally secreted form of human MD-2, e.g., as described by Visintin, Proc. Natl. Acad. Sci. USA 98(21):12156-12161. The chimeric protein can be soluble in aqueous media or be sufficiently hydrophobic to be lipid soluble, e.g., partially soluble in a liposome. The chimeric protein or variant MD-2 can be glycosylated. The MD-2 polypeptide can comprise a homodimer or a heterodimer, e.g., a homodimeric MD-2. The MD-2 polypeptide can comprise an amino terminal fragment of the MD-2 polypeptide, e.g., as described herein.

In one aspect, chimeric protein or variant MD-2 is a recombinant protein. In one aspect, the chimeric protein or variant MD-2 comprises a peptidomimetic or synthetic protein. The first domain can be joined to the second domain by a chemical linking agent.

The invention provides pharmaceutical compositions comprising a chimeric protein or variant MD-2 of the invention and a pharmaceutically acceptable excipient. The invention provides parenteral formulations comprising a chimeric protein or variant MD-2 of the invention. The invention provides enteral formulations comprising a chimeric protein or variant MD-2 of the invention.

The invention provides methods for treating sepsis comprising: (a) providing a pharmaceutical composition comprising a chimeric protein or variant MD-2 (e.g., a mutant or truncated MD-2) of the invention; and (b) administering an effective amount of the pharmaceutical composition to a subject in need thereof, thereby treating the sepsis. The invention provides methods for treating a condition comprising an lipopolysaccharide (LPS)-induced disease or pathology comprising administering a therapeutically effective amount of a pharmaceutical composition comprising a chimeric protein or variant MD-2 of the invention. The LPS-induced disease or pathology can be selected from the group consisting of endotoxin-induced septic shock, endotoxin-induced toxic shock, sepsis, severe sepsis, septic shock caused by Gram-negative bacteria, bacterial infections, shock, inflammatory diseases, graft versus host disease, autoimmune diseases, acute respiratory distress syndrome, granulomatous diseases, chronic infections, transplant rejection, acute respiratory asthma, viral infections, parasitic infections, fungal infections, and trauma. The invention provides methods for increasing clearance of LPS from circulation using a chimeric protein or variant MD-2 of the invention.

The invention also provides an isolated or recombinant nucleic acid encoding a chimeric protein of the invention, e.g., a fusion protein comprising a first domain comprising an MD-2 polypeptide (e.g., a mutant or truncated MD-2 polypeptide of the invention) and at least one additional domain, e.g., a second or third (or more) domain. In alternative aspects, the additional (e.g., second) domain comprises an opsinizing agent (e.g., an Fc domain), a protein C (e.g., a human activated protein C), an antibacterial or bacteriostatic peptide or protein, an antibiotic, a cytokine, an immunoregulatory agent, an anti-inflammatory agent, a complement activating agent, such as a collagen-like domain or a fibrinogen-like domain (e.g., a ficolin), carbohydrate-binding domains, and the like and combinations thereof—particularly in multidomain aspects of the invention. For example, the invention provides a chimeric protein comprising a multi-cluster (e.g., a pentameric cluster) of Fc domains and at least one MD2 moiety of the invention. The invention also provides expression cassettes, vectors, host cells and transgenic non-human animals and plants comprising these nucleic acids, and methods of making these host cells and transgenic non-human animals and plants.

The invention provides mutant or truncated MD-2 polypeptides, wherein the MD-2 polypeptide specifically binds lipopolysaccharide (LPS) but cannot bind or has decreased binding affinity to toll-like receptor-4 (TLR4). The mutant or truncated MD-2 polypeptide can be a variant of the human MD-2 having a sequence as set forth in SEQ ID NO:1, or a mature form thereof lacking a signal sequence. The mutant or truncated polypeptide can has (a) an amino acid sequence as set forth in SEQ ID NO:37, SEQ ID NO:38, SEQ ID NO:39, or (b) an amino acid sequence wherein one, several or all of the alanines in SEQ ID NO:1 or one, several or all of the alanines in a polyA domain of SEQ ID NO:37, SEQ ID NO:38 or SEQ ID NO:39 are replaced with a valine (val), a leucine (leu), an isoleucine (ile) or another aliphatic amino acid, or glycine, or equivalents, or a combination thereof. The MD-2 polypeptide can comprise a naturally secreted form of human MD-2. In one aspect, the MD-2 polypeptide is glycosylated, or, the MD-2 polypeptide comprises a dimeric MD-2, or, the MD-2 polypeptide comprises an amino terminal fragment of the MD-2 polypeptide. In one aspect, the MD-2 polypeptide comprises a peptidomimetic or synthetic protein.

The invention provides chimeric proteins comprising a first domain comprising an MD-2 polypeptide and at least a second domain, e.g., a chimeric protein comprising a recombinant fusion protein. In one aspect, the additional domain (e.g., the at least second domain) comprises an opsinizing agent, e.g., an antibody Fc domain or an antibody that binds to an Fc receptor. In one aspect, the chimeric protein comprises two or more antibody Fc domains, or, the chimeric protein comprises two or more MD-2 polypeptides. In one aspect, the opsinizing agent comprises a human opsinizing agent. In one aspect, the MD-2 polypeptide comprises a mature MD-2 lacking a signal sequence. In one aspect, the MD-2 polypeptide comprises a human MD-2 polypeptide, or, a mutant or truncated MD-2 polypeptide, e.g., wherein the mutant or truncated polypeptide specifically binds LPS and binds toll like receptor 4 (TLR4) with an affinity less than that of wild type TLR4. In one aspect, the mutant or truncated polypeptide does not bind wild type TLR4. In one aspect, the mutant or truncated polypeptide has (a) an amino acid sequence as set forth in SEQ ID NO:37, SEQ ID NO:38, SEQ ID NO:39, or (b) an amino acid sequence wherein one, several or all of the alanines in SEQ ID NO:1 or one, several or all of the alanines in a polyA domain of SEQ ID NO:37, SEQ ID NO:38 or SEQ ID NO:39 are replaced with a valine (val), a leucine (leu), an isoleucine (ile) or another aliphatic amino acid, or glycine, or equivalents, or a combination thereof. In one aspect, the MD-2 variant has increased affinity for LPS. In one aspect, the MD-2 variant has increased affinity for toll like receptor 4 (TLR4) or CD14. In one aspect, the MD-2 polypeptide comprises a mutation or truncation of a human MD-2 polypeptide. In one aspect, the truncated MD-2 has increased affinity for lipopolysaccharide (LPS), or, the truncated MD-2 has increased affinity for toll like receptor 4 (TLR4) or CD14. In one aspect, the chimeric protein is soluble in aqueous media or the MD-2 polypeptide comprises a naturally secreted form of human MD-2. In one aspect, the chimeric protein is glycosylated, e.g., N- or O-linked glycosylation. In one aspect, the MD-2 polypeptide comprises a dimeric MD-2, or, the MD-2 polypeptide comprises an amino terminal fragment of the MD-2 polypeptide. In one aspect, the at least second domain comprises an Fc domain, a protein C, an antibacterial or bacteriostatic peptide or protein, an antibiotic, a cytokine, an immunoregulatory agent, an anti-inflammatory agent, a complement activating agent, a carbohydrate-binding domain or a combination thereof. In one aspect, the protein C is a human activated protein C. In one aspect, the complement activating agent comprises a collagen-like domain, a fibrinogen-like domain or a ficolin. In one aspect, the chimeric protein is a recombinant protein, or, a peptidomimetic or synthetic protein, or a combination thereof. In one aspect, the first domain is joined to the second domain by a chemical linking agent or an electrostatic attraction.

The invention provides pharmaceutical compositions comprising a mutant or truncated MD-2 polypeptide of the invention or a chimeric protein of the invention, and a pharmaceutically acceptable excipient. The invention provides parenteral or enteral, oral or topical formulations comprising a mutant or truncated MD-2 polypeptide of the invention or a chimeric protein of the invention, and a pharmaceutically acceptable excipient.

The invention provides methods for treating or ameliorating sepsis comprising: (a) providing a pharmaceutical composition comprising a mutant or truncated MD-2 polypeptide of the invention or a chimeric protein of the invention; and (b) administering an effective amount of the pharmaceutical composition to a subject in need thereof, thereby treating the sepsis. The invention provides methods for treating or ameliorating a condition comprising an LPS-induced disease, infection or pathology comprising administering a therapeutically effective amount of a pharmaceutical composition comprising a mutant or truncated MD-2 polypeptide of the invention or a chimeric protein of the invention. In one aspect, the LPS-induced disease or pathology is selected from the group consisting of endotoxin-induced septic shock, endotoxin-induced toxic shock, sepsis, severe sepsis, septic shock caused by Gram-negative bacteria, bacterial infections, shock, inflammatory diseases, graft versus host disease, autoimmune diseases, acute respiratory distress syndrome, granulomatous diseases, chronic infections, transplant rejection, acute respiratory asthma, viral infections, parasitic infections, fungal infections, and trauma.

The invention provides methods for decreasing the amount of endotoxin in a body fluid comprising: (a) providing a composition or formulation comprising a mutant or truncated MD-2 polypeptide of the invention or a chimeric protein of the invention; and (b) administering an effective amount of the composition or formulation to a subject in need thereof, thereby decreasing the amount of endotoxin in the body fluid. In one aspect, the body fluid comprises blood, serum or CSF.

The invention provides isolated or recombinant nucleic acids encoding a mutant or truncated MD-2 polypeptide of the invention or a chimeric protein of the invention. The invention provides isolated or recombinant nucleic acids encoding a chimeric protein comprising a first domain comprising an MD-2 polypeptide and a second domain comprising an opsinizing agent. The invention provides vectors or expression cassettes comprising the isolated or recombinant nucleic acid of the invention.

The invention provides host cells comprising a vector or expression cassette of the invention and/or a nucleic acid of the invention. In one aspect, the cell is a bacterial cell, a mammalian cell, a fungal cell, an insect cell, a yeast cell or a plant cell.

The invention provides non-human transgenic animals (e.g., mice, rats, rabbits, and the like) comprising a vector or expression cassette of the invention and/or a nucleic acid of the invention.

The invention provides composition for transfecting nucleic acids into a cell comprising: a mutant or truncated MD-2 polypeptide of the invention, and/or, a chimeric protein of the invention; lipopolysaccharide (LPS); and, a nucleic acid. In one aspect, the nucleic acid comprises naked DNA or RNA, and optionally the naked DNA or RNA is operably linked to a promoter. In one aspect, the nucleic acid comprises plasmid DNA, an expression cassette or a vector such as an expression vector. In one aspect, the lipopolysaccharide (LPS) comprises a bacterial lipopolysaccharide (LPS) or synthetic LPS, or a combination thereof. In one aspect, the composition for transfecting nucleic acids further comprises a lipopolysaccharide-binding protein (LBP) and/or a CD14 polypeptide, e.g., human forms of LBP or CD14. In one aspect, the cell is a bacterial cell or a mammalian cell, wherein optionally the mammalian cell is a human cell.

The invention provides methods for transfecting a cell with nucleic acid comprising the following steps: (a) providing a nucleic acid-comprising composition of the invention (for transfecting nucleic acids); (b) contacting the cell with the composition of step (a) under conditions wherein the composition is internalized into the cell. In one aspect, the transfecting is an in vivo transfection or an in vitro transfection.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 4 illustrates the human MD-2 alanine replacement mutants (SEQ ID NOS:3-35) of the invention, as described in detail in Example 1, below.

FIGS. 9A and 9B illustrates sMD-2 mutant binding to TLR4, as described in detail in Example 1, below.

Like reference symbols in the various drawings indicate like elements.

DETAILED DESCRIPTION

Figure 1:
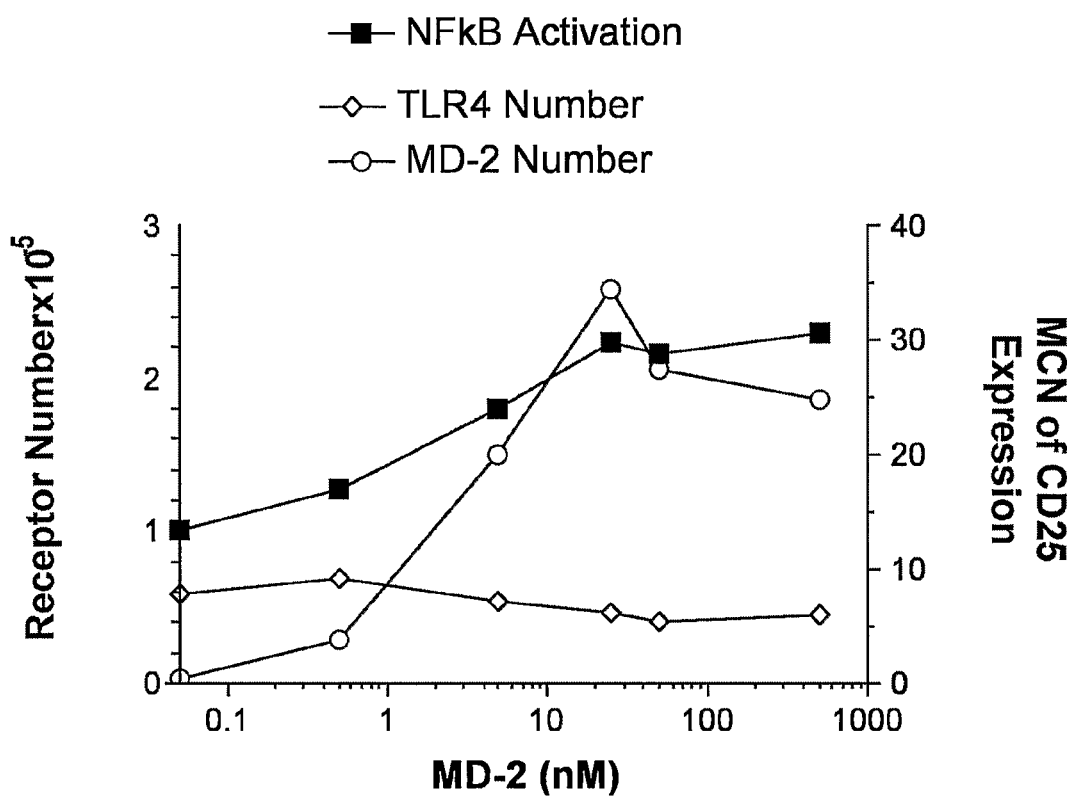
FIG. 1 shows the effect of cell surface level of MD-2 on LPS activation, as described in detail in Example 1, below.

The invention provides compositions and methods for the treatment of sepsis caused by infectious diseases, such as bacterial and fungal diseases. In one aspect, the invention provides variant MD-2 polypeptides and methods of using them, e.g., as bacteria-targeting agents for delivering compositions to microorganisms, for example, their use as antibacterial agents and to treat sepsis. The invention also provides information about the structure and function of both membrane and soluble MD-2 using different mutational strategies as well as using different cell lines and highly purified soluble proteins.

In one aspect, the invention is directed to chimeric proteins comprising the MD-2 polypeptide and an opsinizing agent, e.g., antibody Fc domains, or equivalent. In one aspect, the invention is directed to chimeric proteins comprising fragments or altered form of MD-2 polypeptide and antibody Fc domains, or equivalent. The invention also provides pharmaceutical compositions comprising the chimeric polypeptides of the invention, and methods of making and using them, including methods for ameliorating or preventing sepsis.

Using site directed mutagenesis, it was found that glycosylation has no effect on MD-2 function as membrane protein but slightly impairs soluble MD-2. Alanine scanning was used for mutagenesis experiments to identify regions of human MD-2 that are important for TLR4 and LPS binding. We found that mutation in the N-terminal 61 amino acids of MD-2 did not abolish LPS activation of CHO cells co-transfected with TLR4 and MD-2. The residues 79-83, 121-125 and 125-129 of MD-2 are identified as important in LPS activation but not surface expression of membrane MD-2. The structure of soluble MD-2 is more sensitive to mutation than membrane MD-2. Our results demonstrate that more than one region of soluble MD-2 binds to TLR4. At least one binding site for TLR4 is not involved in LPS binding but affects oligomerization of soluble MD-2. Another TLR4 binding site is adjacent to LPS binding site. The invention identifies a novel LPS binding region of monomeric soluble MD-2 to a cluster of basic residues 121-131 of human MD-2 (SEQ ID NO:1) and a TLR4 binding site to residues 130-131 of human MD-2 (SEQ ID NO:1). These studies also demonstrate that the structure/function relationship of membrane MD-2 and soluble MD-2 are somewhat different.

Human MD-2 (SEQ ID NO:1) used in the compositions or methods of the invention can have the sequence (where the bolded MLPFLFFSTLFSSIFT (SEQ ID NO:36) is the signal peptide):

```
Signal peptide: MLPFLFFSTLFSSIFT (SEQ ID NO: 36)

MLPFLFFSTLFSSIFTEAQKQYWVCNSSDASISYTYCDKMQYPISINVNP

CIELKGSKGLLHIFYIPRRDLKQLYFNLYITVNTMNLPKRKEVICRGSDD

DYSFCRALKGETVNTTISFSFKGIKFSKGKYKCVVEAISGSPEEMLFCL

EFVILHQPNSN (SEQ ID NO:1)
```

Or, the human MD-2 (SEQ ID NO:1) used in the compositions or methods of the invention can have a sequence without a signal peptide:

```
            "mature protein"
1           10         20         30         40
EAQKQYWVCN  SSDASISYTY CDKMQYPISI NVNPCIELKG SKGLLHIFYI 50          60         70         80         90
PRRDLKQLYF  NLYITVNTMN LPKRKEVICR GSDDDYSFCR ALKGETVNTT 100         110        120        130        140
ISFSFKGIKF  SKGKYKCVVE AISGSPEEML FCLEFVILHQ PNSN (beginning at residue 17 to 143 of SEQ ID NO:1)
EAQKQYWVCNSSDASISYTYCDKMQYPISINVNPCIELKGSKGLLHIFYIPRRDLKQLYF

NLYITVNTMNLPKRKEVICRGSDDDYSFCRALKGETVNTTISFSFKGIKFSKGKYKCVVE

AISGSPEEMLFCLEFVILHQPNSN (SEQ ID NO: 40)
```

Human MD-2 (SEQ ID NO:1) with or without a signal peptide, or with or without various domains, such as an LPS and/or TLR4 binding domain, can be encoded by, e.g., the nucleic acid sequence SEQ ID NO:2 or subsequences or variations (e.g., degenerate forms, RNA, PNAs) thereof:

See, e.g., Shimazu (1999) J. Exp. Med. 189 (11), 1777-1782; Miyake (2000) J. Endotoxin Res. 6(5):389-91; and, Genbank accession no. AB018549.

The invention also provides MD-2 mutants (including sequence mutants, e.g., the polyA mutants or equivalents thereof) or truncated forms that can bind LPS but not TLR4. Because assays that screen for LPS and TLR4 specific binding are well known in the art, all MD-2 mutants (including sequence mutants, e.g., the polyA mutants or equivalents thereof) or truncated forms that can bind LPS but not TLR4 are within the scope of the invention.

The invention also provides mutants of MD-2, including the following "alanine scanning" mutants (and equivalents thereof), which indicates polyA residues replacing wild type human MD-2 amino acid residue sequence—the polyA sequence is listed above the human MD-2 amino acid residue sequence it replaces (SEQ NOs: 3-35; for example, SEQ ID NO:3 is the processed, or "mature" human MD2 SEQ ID NO:1 without its signal sequence, as described, above, except that residues 26 to 29 are alanines; SEQ ID NO:4 is the "mature" human MD2 SEQ ID NO:1, except that residues 32 to 36 are alanines; SEQ ID NO:5 is the "mature" human MD2 SEQ ID NO:1, except that residues 42 to 46 are alanines; SEQ ID NO:6 is the "mature" human MD2 SEQ ID NO:1, except that residues 19 to 23 are alanines, etc. . . . with SEQ ID NO:35 is the "mature" human MD2 SEQ ID NO:1, except that residues 156 to 160 are alanines):

```
                                                  (SEQ ID NO:2)
  1 ggcggccgc tcccacttcg gcacgagggg cacgaggtaa atcttttctg cttactgaaa 61 aggaagagtc tgatgattag ttactgatcc tctttgcatt tgtaaagctt tggagatatt 121 gaatcatgtt accatttctg ttttttttcca ccctgttttc ttccatattt actgaagctc 181 agaagcagta ttgggtctgc aactcatccg atgcaagtat tcatacacc tactgtgata 241 aaatgcaata cccaatttca attaatgtta acccctgtat agaattgaaa ggatccaaag 301 gattattgca cattttctac attccaagga gagatttaaa gcaattatat ttcaatctct 361 atataactgt caacaccatg aatcttccaa agcgcaaaga agttatttgc cgaggatctg 421 atgacgatta ctcttttgc agagctctga agggagagac tgtgaataca acaatatcat 481 tctccttcaa gggaataaaa ttttctaagg gaaaatacaa atgtgttgtt gaagctattt 541 ctgggagccc agaagaaatg ctctttttgct tggagtttgt catcctacac caacctaatt 601 caaattagaa taaattgagt attt
```

```
          aaaa  aaaaa      AAAAA
  AAAAA        AAAAA      AAAAA    AAAAA
EAQKQYWVCNSSDASISYTYCDKMQYPISINVNP
17 20          30         40         50 aaaaa
        aaaaa   aaaaa aaaaa      aaaaa  aaaaa
   aaaaa       AAAAA   AAAAA  AAAAA     AAAAA
CIELKGSKGLLHIFYIPRRDLKQLYFNLYITVNTMNLPKRKEVICRGSDDDYSF
51         60         70        80         90        100 aaaaa                                   aaaaa
   aaaaa  aaaaa  aaaaa           aaaaa aaaaa  AAAAA
   aaaaa  AAAAA     AAAAA  AAAAA  aaaaa       AAAAA  AAAAA
CRALKGETVNTTISFSFKGIKFSKGKYKCVVEAISGSPEEMLFCLEFVILHQPNSN
105    110       120        130        140       150        160
```

Exemplary MD2 variants of the invention comprise the following alanine scanning "therapeutic" mutant sequences that do not bind TLR4 but do bind LPS (see bolded polyA residues, above):

```
polyA "therapeutic" mutant at residues 42-46
                                         (SEQ ID NO:37)
EAQKQYWVCNSSDASISYTYCDKMQAAAAANVNPCIELKGSKGLLHIFYI
PRRDLKQLYFNLYITVNTMNLPKRKEVICRGSDDDYSFCRALKGETVNTT
ISFSFKGIKFSKGKYKCVVEAISGSPEEMLFCLEFVILHQPNSN polyA "therapeutic" mutant at residues 79-83
                                         (SEQ ID NO:38)
EAQKQYWVCNSSDASISYTYCDKMQYPISINVNPCIELKGSKGLLHIFYI
PRRDLKQLYFNLAAAAATMNLPKRKEVICRGSDDDYSFCRALKGETVNTT
ISFSFKGIKFSKGKYKCVVEAISGSPEEMLFCLEFVILHQPNSN polyA "therapeutic" mutant at residues 125-129
                                         (SEQ ID NO:39)
EAQKQYWVCNSSDASISYTYCDKMQYPISINVNPCIELKGSKGLLHIFYI
PRRDLKQLYFNLYITVNTMNLPKRKEVICRGSDDDYSFCRALKGETVNTT
ISFSFKGIAAAAAKYKCVVEAISGSPEEMLFCLEFVILHQPNSN
```

In alternative aspects of the invention, one, several or all of the alanines, including the polyA domains of SEQ ID NO:37, SEQ ID NO:38, SEQ ID NO:39, are replaced with a valine (val), a leucine (leu), an isoleucine (ile) or another aliphatic amino acid, or glycine, or equivalents, or a combination thereof (natural or synthetic).

Definitions

Unless defined otherwise, all technical and scientific terms used herein have the same meaning as is commonly understood by one of skill in the art to which the invention(s) belong. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

The term "antibody" includes a peptide or polypeptide derived from, modeled after or substantially encoded by an immunoglobulin gene or immunoglobulin genes, or fragments thereof, capable of specifically binding an antigen or epitope, see, e.g. *Fundamental Immunology*, Third Edition, W. E. Paul, ed., Raven Press, N.Y. (1993); Wilson (1994) *J. Immunol. Methods* 175:267-273; and Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR). Single chain antibodies are also included by reference in the term "antibody."

The term "treatment" as used herein refers to partially or completely ameliorating at least one symptom of, partially or completely treating or curing and/or preventing the development of a disease or a condition, for example, sepsis.

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides, naturally occurring nucleic acids, synthetic nucleic acids, and recombinant nucleic acids. The term also encompasses nucleic-acid-like structures with synthetic backbones, see e.g., Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev* 6:153-156. The term "nucleic acid" as used herein also refers to a deoxyribonucleotide (DNA) or ribonucleotide (RNA) in either single- or double-stranded form. The term encompasses nucleic acids containing known analogues of natural nucleotides. The term encompasses mixed oligonucleotides comprising an RNA portion bearing 2'-O-alkyl substituents conjugated to a DNA portion via a phosphodiester linkage, see, e.g., U.S. Pat. No. 5,013,830. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923-1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug Dev 6:153-156). The term nucleic acid is used interchangeably with gene, polynucleotide, DNA, RNA, cDNA, mRNA, oligonucleotide primer, probe and amplification product.

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

Generating and Manipulating Nucleic Acids and Polypeptides

The invention provides chimeric polypeptides comprising MD-2 polypeptides and an opsinizing agent, e.g., antibodies and specific domains or fragments of antibodies (e.g., Fc domains), and nucleic acids encoding them. The invention can be practiced in conjunction with any method or protocol or device known in the art, which are well described in the scientific and patent literature.

The nucleic acids used to practice this invention, whether RNA, cDNA, genomic DNA, vectors, viruses or hybrids thereof, may be isolated from a variety of sources, genetically engineered, amplified, and/or expressed/ generated recombinantly (recombinant polypeptides can be modified or immobilized to arrays in accordance with the invention). Any recombinant expression system can be used, including bacterial, mammalian, yeast, insect or plant cell expression systems.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

Alternatively, these nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

The nucleic acids used to practice this invention, whether RNA, iRNA, siRNA, antisense nucleic acid, cDNA, genomic DNA, vectors, viruses or hybrids thereof, may be isolated from a variety of sources, genetically engineered, amplified, and/or expressed/ generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., *Molecular Cloning: A Laboratory Manual* (2nd ed.), Vols. 1-3, Cold Spring Harbor Laboratory, (1989); *Current Protocols in Molecular Biology*, Ausubel, ed. John Wiley & Sons, Inc., New York (1997); *Laboratory Techniques in Biochemistry and Molecular Biology: Hybridization with Nucleic Acid Probes*, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., *PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) Proc. Natl. Acad. Sci. USA 86:1173); and, self-sustained sequence replication (see, e.g., Guatelli (1990) *Proc. Natl. Acad. Sci.* USA 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic "variant MD-2" or "chimeric MD-2" composition is within the scope of the invention if it has LPS binding activity (any LPS binding activity, including increased, decrease or the same LPS binding activity as compared to wild type MD-2).

A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a polypeptide, resulting in modification of the structure of the polypeptide, without significantly altering its biological activity. For example, amino- or carboxyl-terminal or internal amino acid residues that are not required for LPS binding activity can be removed. Modified polypeptide sequences of the invention can be assayed for activity (e.g., therapeutic or biological, such as LPS binding activity) by any number of methods, including contacting the modified polypeptide sequence with a substrate (e.g., LPS or TLR4) and determining whether the modified polypeptide binds with the same or a different affinity to the substrate.

The invention provides MD-2 variants comprising conservative amino acid residue substitutions as compared to wild type; and in this aspect conservative amino acid residue substitutions are those that substitute a given amino acid in a polypeptide by another amino acid of like characteristics. In alternative aspects, the invention provides MD-2 polypeptides with the following conservative substitution replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. In alternative aspects, these conservative substitutions can also be synthetic equivalents of these amino acids.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with anunonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercum-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R— or S— form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini.

It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

As discussed above, a variant MD-2 or chimeric protein comprising an MD-2 (e.g., the human MD-2, SEQ ID NO:1) of the compositions of the invention or used in methods of the invention can lack a signal peptide, or can lack its endogenous signal peptide and in its place have a heterologous signal peptide. Additional MD-2 variants of the compositions or used in the methods of the invention are those in which additional amino acids are fused to the polypeptide, such as a leader sequence, a secretory sequence, a proprotein sequence or a sequence which facilitates purification, enrichment, or stabilization of the polypeptide.

In alternative aspects, the MD-2 variant of the invention binds LPS but does not bind TLR-4 (or binds TLR-4 with less affinity than the corresponding wild type MD-2), for example as the exemplary MD-2 variants of the invention having a sequence as set forth in SEQ ID NO:37, SEQ ID NO:38, SEQ ID NO:39. In alternative aspects, the MD-2 variant of the invention has increased affinity for LPS, or, increased affinity for toll like receptor 4 (TLR4), CD14 or LPS, or a combination thereof. In alternative aspects, the MD-2 variant of the invention comprises a truncation of a human MD-2 polypeptide, e.g., as described herein, or, e.g., by Re (2003) J. Immunol. 171(10):5272-5276. In one aspect, the truncated MD-2 has increased affinity for LPS. In alternative aspects, the truncated MD-2 polypeptides of the invention can have increased or decreased affinity for toll like receptor 4 (TLR4) or CD14 or LPS or a combination thereof. Binding assays for toll like receptor 4 (TLR4) or CD14 or LPS with ligands such as MD-2 are considered routine and well known in the art. For example, TLR4 binding assays are well known, as described, e.g., in Schwartz, et al., U.S. patent application no. 20030232352. LPS binding assays and kits for detecting endotoxin are well known, as described, e.g., in U.S. patent applications no. 20020107201; 20030108573; 20040137001; 20050048655; 20050069972; 20040235195. Protein C activity assays are well known, as described, e.g., in U.S. patent applications no. 20050037964; 20040038288; 20040028670.

Pharmaceutical Compositions

The invention provides pharmaceutical compositions comprising a chimeric protein or a variant MD-2 (e.g., mutated and/or truncated MD-2) of the invention and a pharmaceutically acceptable excipient. The invention provides parenteral formulations comprising a chimeric or variant MD-2 protein of the invention. The invention provides enteral formulations comprising a chimeric protein or variant MD-2 of the invention. The invention provides methods for treating sepsis comprising providing a pharmaceutical composition comprising a chimeric or variant MD-2 protein of the invention; and administering an effective amount of the pharmaceutical composition to a subject in need thereof, thereby treating the sepsis.

The invention provides methods for decreasing the levels of lipopolysaccharide (LPS) (gram negative endotoxin) in a fluid or liquid—including bodily fluids such as blood, CSF and the like. The method can also be practiced ex vivo or in vitro, or on a non-biological fluid or substance. In this aspect, the method comprises providing a pharmaceutical composition comprising a chimeric or variant MD-2 protein of the invention; and administering an effective amount of the pharmaceutical composition to a subject in need thereof.

The pharmaceutical compositions used in the methods of the invention can be administered by any means known in the art, e.g., parenterally, topically, orally, or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a chimeric polypeptide or peptidomimetic of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of hydrophobic active agents of the invention. Oil-based suspensions can be formulated by suspending an active agent (e.g., a chimeric composition of the invention) in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In the methods of the invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In the methods of the invention, the pharmaceutical compounds can be delivered by transdermally, by a topical route, formulated as applicator sticks, solutions, suspensions, emulsions, gels, creams, ointments, pastes, jellies, paints, powders, and aerosols.

In the methods of the invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In the methods of the invention, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). In the methods of the invention, a pharmaceutical composition is administered in an amount sufficient to treat (e.g., ameliorate) or prevent sepsis or other LPS-related conditions, diseases or symptoms, or to decrease the amount of endotoxin (LPS) in a fluid, e.g., a body fluid such as blood, serum, CSF and the like. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat the treat (e.g., ameliorate) or prevent sepsis or other LPS-related conditions, diseases or symptoms. For example, an exemplary pharmaceutical formulation for oral administration of variant MD-2 and/or chimeric protein is in a daily amount of between about 0.1 to 0.5 to about 20, 50, 100 or 1000 or more µg per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The compositions and formulations of the invention can further comprise other drugs or pharmaceuticals, e.g., compositions for treating septic shock, infection, fever, pain and related symptoms or conditions. The methods of the invention can further comprise co-administration with other drugs or pharmaceuticals, e.g., compositions for treating septic shock, infection, fever, pain and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Kits

The invention provides kits comprising compositions of the invention, e.g. the pharmaceutical compositions of the invention, including instructions on practicing the methods of the invention, e.g., directions as to indications, dosages, patient populations, routes and methods of administration.

The invention will be further described with reference to the following examples; however, it is to be understood that the invention is not limited to such examples.

EXAMPLES

Example 1

The following example describes making and using exemplary compositions of the invention.

Reagents.

*Salmonella minnesota* Re 595 LPS (Re LPS) was prepared as previously described by Viriyakosol (1995) J. Biol. Chem. 270:361. Recombinant soluble CD14 with C-terminal his-tags were prepared as described by Viriyakosol (2000) J. Biol. Chem. 275:3144. Anti His-tag and anti HA-tag was from Qiagen and Roche Diagnostic Corp. Control mouse IgG1 and rabbit IgG were obtained from Caltag. All protein biotinylations were done using the EZ-Link Sulfo-NHS-LC™ Biotinylation Kit (Pierce). All reagents were tested for lipopolysaccharide (LPS) contamination with Limulus Amoebocyte Lysate (BioWhittaker). When necessary, LPS was removed from the reagents using END-X™ (Associates of Cape Cod, Inc.).

Mutagenesis of MD2 Gene.

The human MD2 gene with the gp64 signal peptide sequence as described by Viriyakosol (2001) J. Biol. Chem. 276:38044, was subcloned into the EcoRI and AgeI site of the plasmid pcDNA4/V5His (Invitrogen) for expression of secreted c-terminal His-tag protein in mammalian cells. The MD-2 amino acids were changed using QUICKCHANGE™ Site-Directed Mutagenesis Kit (Stratagene). The mutant MD-2 constructs were transfected into CHO cell line stably transfected with TLR4 containing N-terminal HA-tag and CD25 reporter plasmid as described by Viriyakosol (2001) J. Biol. Chem. 276:38044. Stably transfected cell lines were generated by selection with Zeocin followed by inmunomagnetic sorting using anti-His-tag Mab (Qiagen).

Cell Culture and Transfection.

Cell lines were maintained in the laboratory as previously described by Viriyakosol (1995) J. Biol. Chem. 270:361. CHO cell line stably transfected with inducible membrane CD25 under the transcriptional control of a human E-selectin promoter containing NF-κB binding sites was a gift from Dr. D. Golenbock, as described by Delude (1998) J. Immunol. 161-3001. Plasmid DNA was prepared using an ENDOFREE™ kit (Qiagen). Stably transfected cell lines were generated using LIPOFECTAMINE 2000™ (Life Technologies) according to the manufacture's protocol. The cells expressing TLR proteins were sorted by immunomagnetic beads (Dynal) using anti-HA Mab (Roche Diagnostic Corp.). The stably transfected lines were generated by selection with G418 (Life Technologies). Transfected cells were assayed for surface expression of the HA-epitope by FACS analysis using anti-HA Mab followed by F(ab)'2 fragment of goat anti-mouse Ig-FITC (Caltag).

Analysis of NF-κB Activity by Flow Cytometry.

CHO cells carrying NF-κB reporter plasmids to express surface CD25 were plated in a 24 well plate one day prior to the activation. The cells were stimulated overnight, harvested and stained with PE-CD25 Mab (Becton Dickinson and analyzed by FACS as previously described by Viriyakosol (2001) J. Biol. Chem. 276:38044.

Expression of Soluble MD-2 and Soluble MD-2/TLR4 Complexes

Wild type and mutant MD-2 genes were subcloned into pBlueBac4.5/V5-His (Invitrogen) or pBac11 (Novagen) and recombinant virus generated as by the manufacturers' protocol. Recombinant virus stock was verified to contain the correct mutation by the method described below. Expressed protein in the insect cell supernatant was purified by Ni-NTA affinity chromatography. Recombinant virus encoding the gene for the extracellular portion of TLR4 with a 6His tag and S-tag has been described. For the production of sMD-2/TLR4 complex, MD-2 and TLR4 recombinant virus were co-infected into Hi5 insect cells and the protein purified on S-tag column as described below. The purity of proteins was determined by Comassie Blue staining of purified protein electrophoresed on a NuPAGE gel (Invitrogen). The protein concentrations were determined by protein BCA assay (Pierce), direct protein ELISA using biotinylated anti His tag, as well as western blotting of the protein with anti His tag.

PCR Analysis of Virus Stock

The viral DNA template was prepared by mixing 10 μl of virus stock with 89 μl lysis buffer (10 mM Tris-HCl, 100 ug/ml gelatin, 0.45% Triton X-100, 0.45% Tween-20, 50 mM KCl, pH 8.3), and 1 μl Proteinase K (6 mg/ml in water). The mixture was incubated for 1 hour at 60° C. and for 10 min at 95° C. to inactivate the Proteinase K. 10 μl of the above reaction was used as a template in a 100 μl PCR to amplify the inserted gene. The resulting fragments were sequenced.

Purification of S-Tag Proteins Using S-Protein Agarose

The harvested Hi5 media was run through a column of S-protein agarose (Novagen) using 0.75 ml agarose per liter of media. The column was washed three times with 20 mM Tris-HCl, 150 mM NaCl, 0.1% Triton X-100, pH 7.5 and then once PBS. The column was eluted with 0.2M citric acid, pH 2.0, which was collected in 1 ml aliquots, neutralized with 700 μl 1M Tris, pH 9.0.

Gel Filtration Chromatography.

The separation was performed on a Rainin Rabbit HPLC system. The sample, 100 μl of purified MD-2 at a concentration of 1.5 mg/ml in PBS, was injected into a 300×7.8 mm Bio-Sil SEC-250 column (Bio-Rad) with a 80×7.8 mm guard column and eluted with PBS containing 0.01% Na Azide at the rate of 1 ml per min.

LPS Binding Assays

Assay for MD-2 binding using immobilized LPS was done similarly to the method described previously by Viriyakosol (2001) J. Biol. Chem. 276:38044.

Activation of U373 Cells.

The cells were cultured in a 96 well plate and activated with various reagents in MEM Earles medium supplemented with 10 mg/ml human serum albumin. The supernatant was harvested after 16 hr of activation and assayed for IL-6 by ELISA as described by Viriyakosol (2001) J. Biol. Chem. 276:38044.

Analysis of sMD-2 Binding to TLR4.

TLR4 transfected CHO cells with or without the CD25 reporter gene were incubated with various concentration of MD-2 in RPMI with 10% FCS for 15 min or 16 hr at 20.degree. C. After washing off the excess protein with the medium, the cells were stained with Mab anti-his (Qiagen) to detect MD-2 or anti-HA to detect TLR4, followed by rabbit anti mouse-Ig-FITC and analyzed by FACS. To quantitate the amount of MD-2 and TLR4 on cell surface, the MCN of fluorescence intensity was compared to the standard curve of SIMPLY CELLULAR™ Microbeads (Bangs Laboratories) stained with the corresponding antibodies.

Results

MD-2 Regulates Levels of LPS Activation.

LPS activation increased with increasing MD-2 levels on the cell surface. TLR4 transfected EL-1 cells (a CHO cell line stably transfected with NF-.kappa.B/CD25 reporter plasmid) were incubated with various amount of soluble MD-2 for 20 min. The amount of soluble MD-2 that bound to TLR4 transfected cells as well as the TLR4 expression level were assayed by FACS analysis using antibody to His-tag and HA-tag, respectively. The MD-2 and TLR4 receptor numbers were calculated by converting mean channel number (MCN) of fluorescence intensity using the standard curve generated with SIMPLY CELLULAR™ Microbeads. The cells were also activated with 100 ng/ml LPS and NF-.kappa.B activation assayed by FACS analysis of surface CD25 expression.

FIG. 1 shows the effect of cell surface level of MD-2 on LPS activation. Various concentrations of sMD-2, plotted on the x-axis, was added to CHO (EL1) cells stably transfected with TLR4. The amount of TLR4 and MD-2 on the cell surface was analyzed by FACS using anti-HA tag and anti-His tag antibody, respectively. The receptor numbers plotted on the left Y-axis were calculated from mean channel number (MCN) and the standard curves generated by simply cellular microbeads. The cells were also activated with 100 ng/ml of LPS. The right Y-axis shows NF-kB activation as MCN of CD25 surface expression analyzed by FACS.

FIG. 1 shows the correlation of MD-2 receptor number with LPS induced NF-κB activation in TLR4 transfected cells, as measured by mean channel number (MCN) of membrane CD25 expression at each concentration of sMD-2 added to TLR4 transfected cells. As the sMD-2 concentration increased, more MD-2 can be detected on the cell surface while TLR4 receptor number remained constant. At a concentration of 0.5 nM sMD-2, the calculated ratio of surface MD-2 per TLR4 was 0.5, yet LPS induced NF-κB activation occurred. The level of activation increased with more MD-2 on the cell surface and reached a maximum when the calculated ratio of MD-2 per TLR4 was approximately 5. Depending upon the level of TLR4 expression, as many as 16 molecules of sMD-2 can bind to each molecule of membrane TLR4.

N-link Glycosylation of Membrane MD-2 has Little Effect on Cellular Activation

Figure 2A:
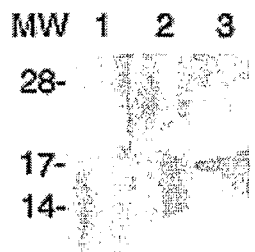
FIGS. 2A and 2B illustrate the expression of the unglycosylation mutant of MD-2, as described in detail in Example 1, below.

Human MD-2 protein has 2 N-glycosylation sites at amino acids N26 and N114. These 2 asparagine residues were mutated by replacing them with glutamines (Q). The mutated MD-2 gene in pcDNAV5His was transfected into TLR4/CHO reporter cell line and a stably transfected cell line was made. This cell line (TLR4/MD-2 NQ) expressed unglycosylated MD-2 protein as shown by western blotting of the cellular extract with antibody to His-tag, as illustrated in FIG. 2A. The TLR4/MD-2 NQ expressed MD-2 protein as a 17 Kd protein while the wild type expressed glycoforms of ~20-27 Kd.

FIG. 2 illustrates the expression of the unglycosylation mutant of MD-2. FIG. 2A:CHO (EL1) cells was stably transfected with TLR4 (lane1), TLR4 and MD-2 wild type (lane 2), TLR4 and MD-2 unglycosylated mutant NQ (lane 3). The cells were lysed and cell extracts immunoprecipitated with Mab against MD-2, SH10. Immuno-precipitates were western blotted and probed with anti-His tag antibody.

Figure 2B:
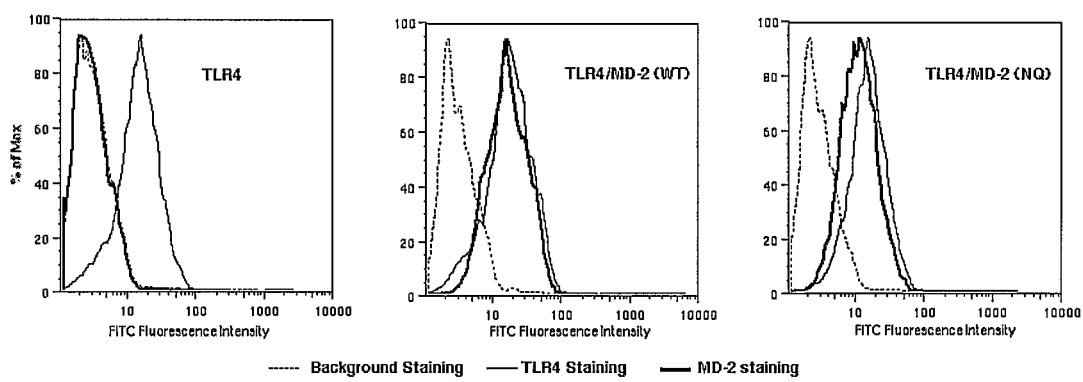

FIG. 2B: Surface expression level of these cell lines were analyzed by FACS using anti-HA tag and anti-His tag staining for TLR4 and MD-2, respectively.

Since the level of MD-2 expression on the cell surface influences LPS activation, it was important to compare the function of this mutant to the wild type expressed at a similar level of MD-2 level. The TLR4/MD-2 NQ cell line was sorted several times by immunomagnetic beads to obtain the cells with comparable expression level to the TLR4/MD-2 wild type (WT) cells. FIG. 2B shows FACS analysis of surface expression of the TLR4 and MD-2 on the TLR4/MD-2 NQ and the WT cell lines. The TLR4/MD-2 NQ and WT cell lines were activated with LPS and NF-κB activation was assayed by CD25 surface expression.

Figure 3A:
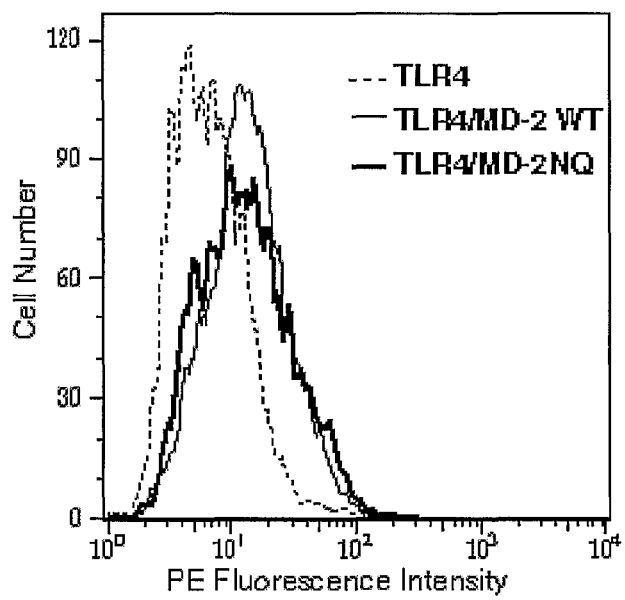
FIGS. 3A and 3B illustrate data showing that the unglycosylated mutant of MD-2 functions normally, as described in detail in Example 1, below.
Figure 3B:
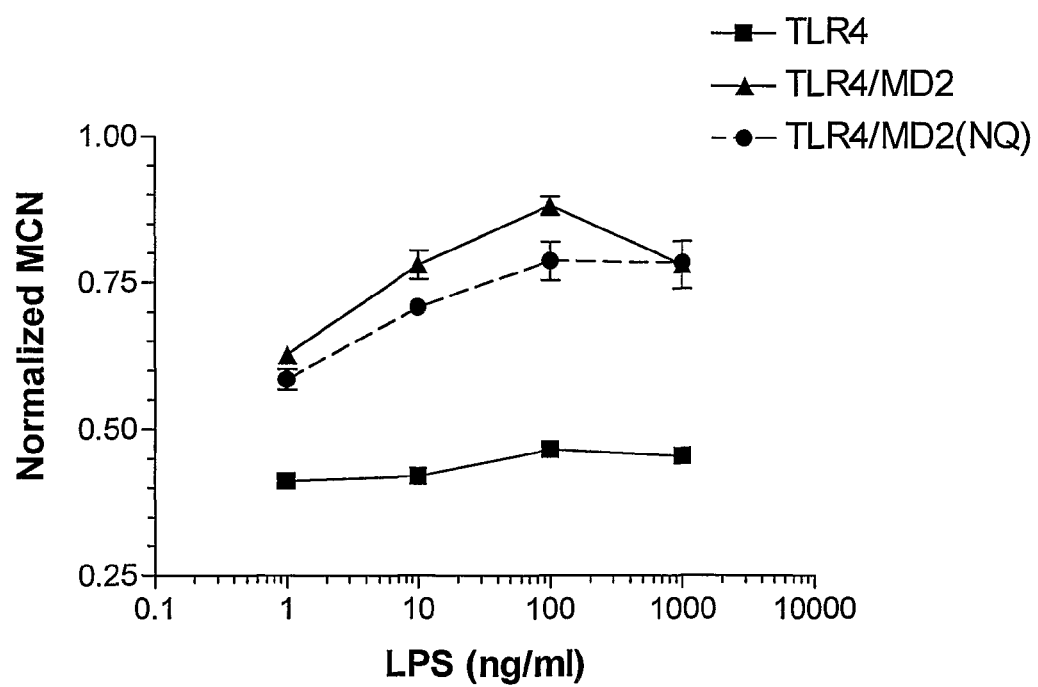

FIG. 3 illustrates data showing that the unglycosylated mutant of MD-2 functions normally. FIG. 3A. CHO (EL1) cells stably transfected with TLR4 (dotted line), TLR4/MD-2 wild type (solid line) and TLR4/MD-2 NQ (bolded line) was stimulated with 100 ng/ml of LPS and NF-kB activation assayed by FACS analysis of CD25 surface expression using anti-CD25-PE. FIG. 3B. Stably transfected CHO (EL1) cells with TLR4 (■), TLR4/MD2 WT (▲) and TLR4/MD2 NQ (●) were activated with various doses of LPS and NF-kB activation assayed by FACS analysis of CD25 surface expression. MCN of fluorescence intensity was normalized by MCN of CD25 expression of cells activated with 100 ng/ml IL-1β. Data are presented as means±SD of duplicate samples.

FIG. 3A shows that 100 ng/ml of LPS activated the non-glycosylated mutant cells to express surface CD25 at the same level as the WT cells. We compared the MCN of fluorescent intensity of CD25 expression after both cell lines were activated with several doses of LPS stimulation from 1 ng/ml to 1 µg/ml and found similar LPS activation level as shown in FIG. 3B. These data show that glycosylation is not important for the LPS receptor function of membrane MD-2.

Critical Regions of Human Membrane MD-2 for TLR4 Binding and Cellular Activation by LPS Regions of functionally importance of human MD-2 were analyzed by site directed mutagenesis. The protein sequence of human MD-2 was analyzed for Kyte-Dolittle hydrophilicity profile with MCVECTOR™ Software. Mutagenesis was designed by replacing a block of 4 to 5 amino acids with alanine as shown in FIG. 4. FIG. 4 illustrates the human MD-2 alanine replacement mutants of the invention. The amino acid sequence of the predicted mature MD-2 protein, starting at amino acids 17, is shown in grey. The 7 Cysteine residues are shown in black. The two N-glycosylation sites are underlined. A set of 4 to 5 alanines replaces the wild type residues in the positions shown above. The blocks of alanine shown in underlined letters replace the hydrophilic regions of MD2 while the ones shown in italics replace the hydrophobic regions. The alanines in lower case letters replace the regions in between.

Figure 5A:
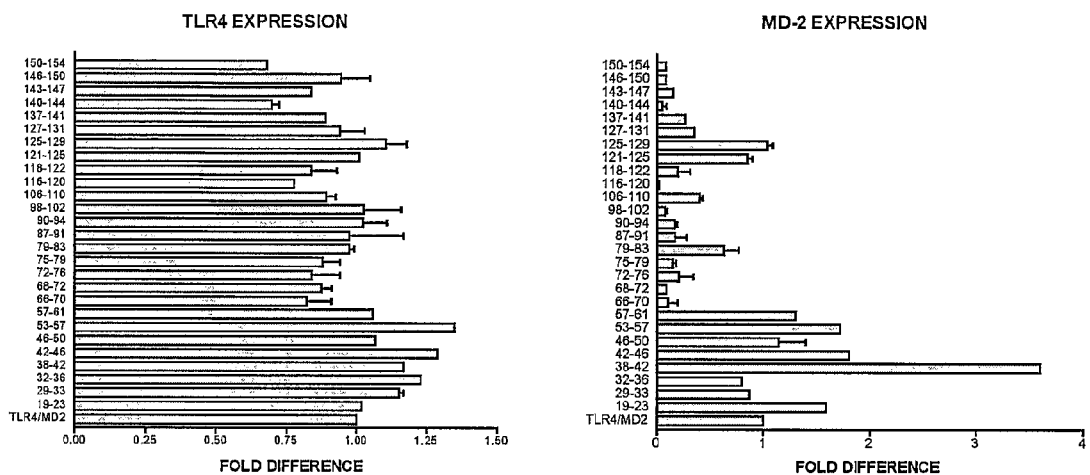
FIGS. 5A and 5B illustrate data showing analyses of membrane MD-2 mutants, as described in detail in Example 1, below.
Figure 5B:
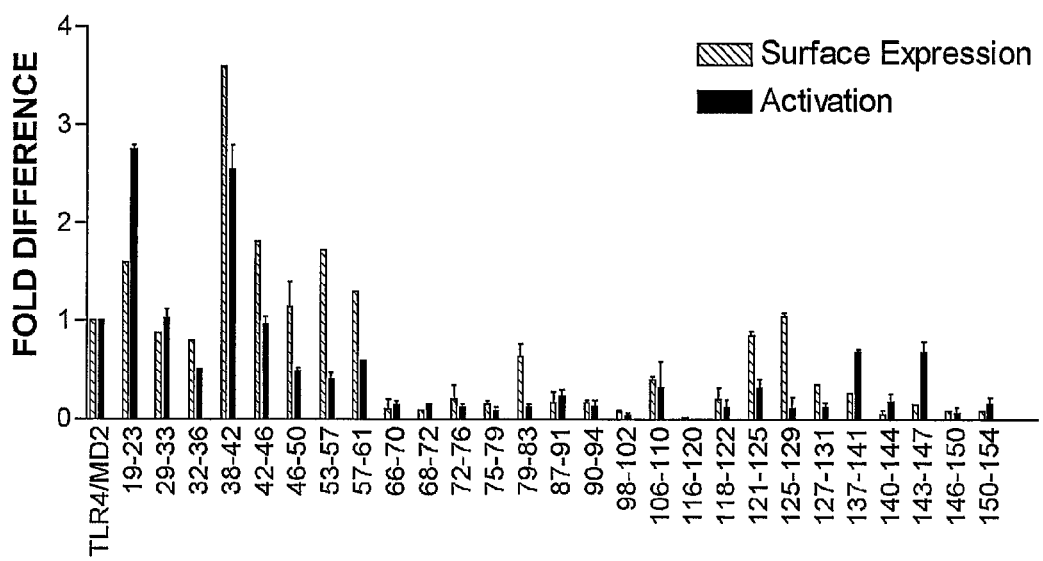

FIG. 5 illustrates data showing analyses of membrane MD-2 mutants. FIG. 5A. Mutant MD-2 in pcDNA V5-His were created by alanine replacement mutagenesis at the amino acid numbers and sequences as indicated and transfected into TLR4/EL1 cells. Expression of TLR4 (left panel) and MD-2 (right panel) on the cell surface were analyzed by FACS using anti HA and anti His, respectively. MCN of fluorescent intensity of the staining was expressed as fold difference of the TLR4/MD-2 wild type. Data are presented as the mean±SD from at least two experiments. FIG. 5B. Stably transfected EL1 cells with TLR4 and MD-2 mutants were activated with 100 ng/ml LPS and NF-κB activation assayed by FACS analysis of surface CD25 staining. MCN of LPS induced CD25 expression was normalized against IL-1β induced CD25 expression. The data comparing fold differences of the wild type of MD-2 surface expression, as shown in A (right panel), and LPS induced CD25 expression are presented as the mean±SD from at least two experiments. The expression constructs with C-terminal His-tags were stably transfected into TLR4/EL1 cells. Cell surface TLR4 and MD-2 by FACS was analyzed using anti HA-tag (FIG. 5A, left panel) and anti His-tag (FIG. 5A, right panel), respectively.

In general, TLR4 expression level correlated with the level of MD-2 expression. Alanine replacement mutagenesis in the N-terminal 61 amino acids of MD-2 produced mutants that expressed equally well or better than the wild type. Mutation in the rest of molecule yielded protein that was expressed poorly on the cell surface except for 3 regions; amino acids 79-83, 106-110 and 121-129. This demonstrates that most of the MD-2 sequence after amino acid 61 is important for cell surface expression. All TLR4/MD-2 mutant cell lines produced variable amount of soluble MD-2 as assayed by ELISA.

The stably transfected cells expressing TLR4 and MD-2 mutants were activated with 100 ng/ml LPS and NF-κB activation assayed by CD25 expression. Each mutant was assayed in duplicate at least twice. FIG. 5B shows the LPS activation levels of different mutants as compared to the surface expression level. None, except the mutant at the hydrophobic residues 29-33, is similar to the WT. All mutants in the N-terminal 61 amino acids, which expressed well on the cell surface, were responsive to LPS. Among this group, mutant 19-23 is more responsive to LPS than one would predict from the surface expression level. Mutant in the region 42-61 expressed better but responded less than half of the WT. The 3 mutants at the C-terminal of this region (amino acids 70-83, 121-125 and 125-129) expressed well but were not responsive to LPS. Mutants in the regions 66-79, 87-102, 116-122 and 127-150 did not express well on the cell surface. Mutants that expressed well on the cell surface but were not activatable by LPS are 79-83, 125-129 and 127-131.

Characteristics of Soluble MD-2 Wild Type (WT)

To further define functional regions of MD-2, soluble MD-2 was expressed from WT and selected mutant constructs. The proteins were purified by Ni-NTA chromatography. Soluble MD-2 WT was first analyzed by gel filtration chromatography.

Figure 6A:
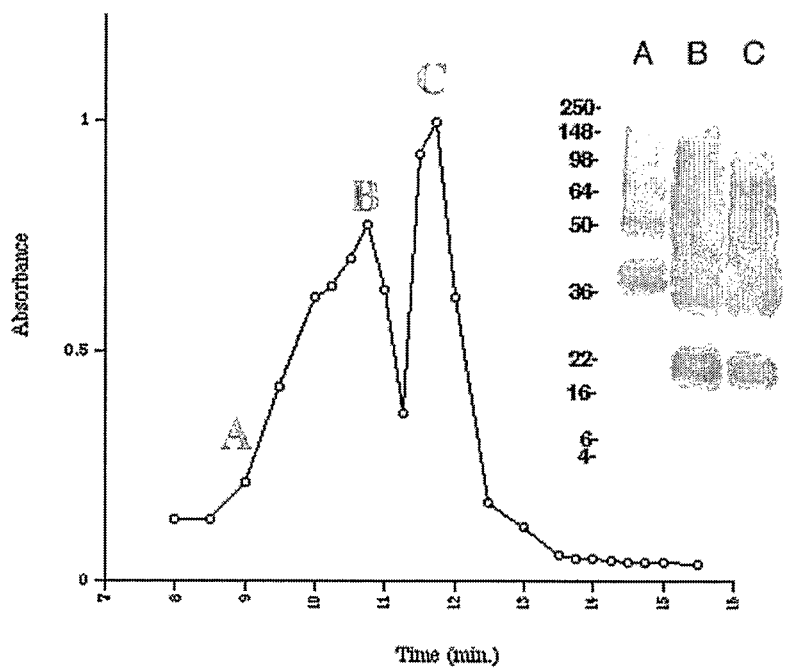
FIGS. 6A, 6B and 6C illustrate the characterization of soluble MD-2, as described in detail in Example 1, below.
Figure 6B:
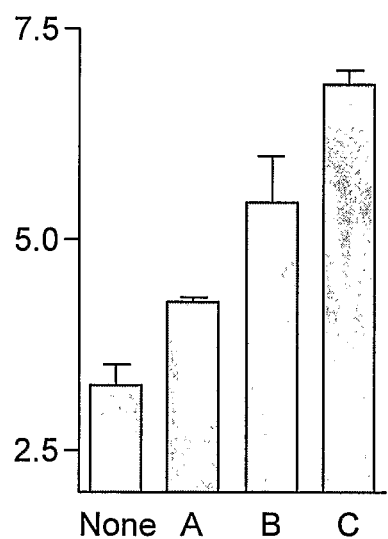
Figure 6C:
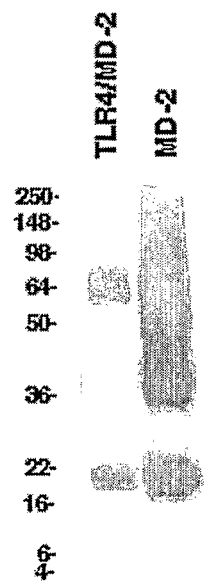

FIG. 6 illustrates the characterization of soluble MD-2. FIG. 6A: Oligomeric state of sMD-2. sMD-2 was chromatographed on a gel filtration HPLC using Bio-Sil SEC250 column and fractions were collected as indicate.(left panel). The oligomeric state of different fractions were analyzed on SDS-PAGE under non-reducing condition and western blotted with anti-His antibody (right panel). FIG. 6B: sMD-2 binding to TLR4. FACS analysis of TLR4-transfected EL1 cells after 15 min incubation with 5 ug/ml of various sMD-2 fractions isolated as shown in A and stained with anti-His tag antibody. FIG. 6C: sMD-2 monomer binds to sTLR4. High Five insect cells were co-infected with both MD-2-His and extracellular TLR4-s-tag-His recombinant virus and the secreted protein purified using s-agarose to capture s-tag. The protein was analyzed on SDS-PAGE under non-reducing condition and western blotted with anti-His antibody.

FIG. 6A shows the chromatogram of sMD-2 separated on a Biosil-SEC 250 column. Two peaks corresponded to molecular weight of 33 and 85.5 Kd (C and B) were observed. We collected protein fractions corresponded to these peaks as well as the flow through fraction. We analyzed these fractions on non-reducing SDS-PAGE and found that they consisted of monomer and oligomers as seen (FIG. 6A). The oligomers can be separated from monomer by gel filtration HPLC but pure monomer was not obtained by this technique. We observed no difference in the multimerization of MD-2 when expressed with or without serum. We tested these fractions for TLR4 binding by adding the proteins to TLR4 transfected cells and assaying for MD-2 on the cell surface by FACS analysis using anti His-tag antibody. We found that the fraction of lowest MW bound best to TLR4 (FIG. 6B). When MD-2 with C-terminal his-tag was co-expressed with extracellular portion of TLR4 with C-terminal His and S-tag and the protein purified using S-agarose we obtained a soluble TLR4/MD-2 complex. This complex consisted only of MD-2 monomer on non-reducing SDS-PAGE (FIG. 6C). The same result was obtained when purified extracellular TLR4 was mixed with MD-2 and immunoprecipitated with S-agarose. These data demonstrate that soluble MD-2 monomer has a higher affinity to extracellular TLR4 than oligomeric soluble MD-2.

Conformation of Soluble MD-2 Mutants

Figure 7A:
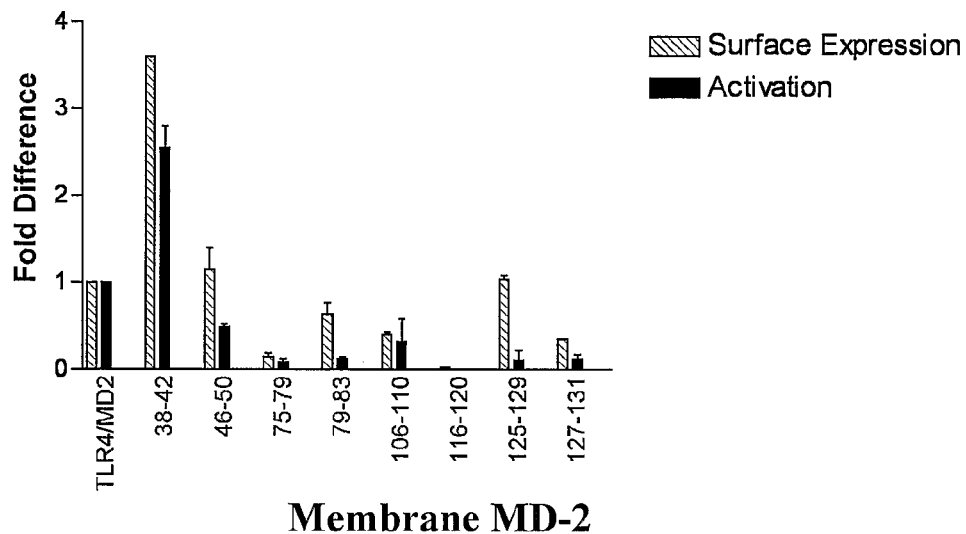
FIGS. 7A and 7B illustrate the effect of alanine substitution and N-glycosylation mutation on sMD-2 oligomerization, as described in detail in Example 1, below.
Figure 7B:
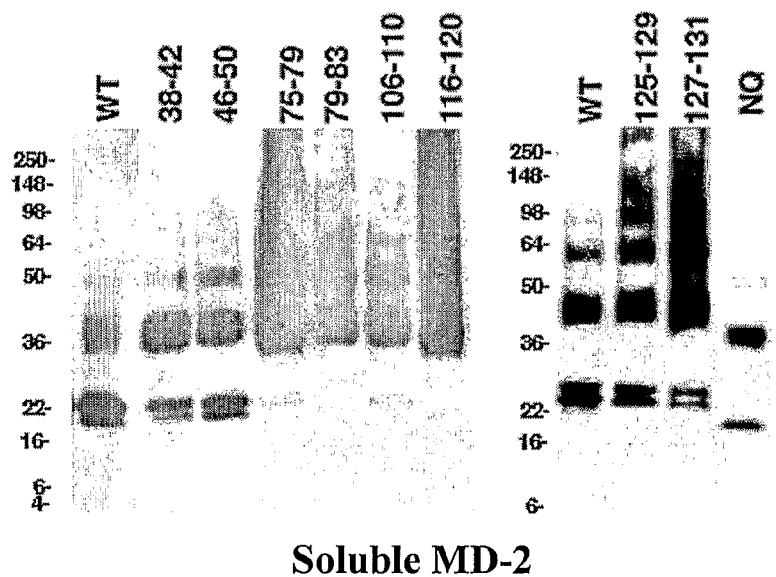

MD-2 mutants were expressed as soluble protein in insect cells and purified them by Ni-NTA affinity chromatography. FIGS. 7A and 7B illustrate the effect of alanine substitution and N-glycosylation mutation on sMD-2 oligomerization. Soluble proteins from selected mutations as shown in the top panel (FIG. 7A) were expressed and purified from insect cells. sMD-2 wild type (WT) and mutant proteins were analyzed on SDS-PAGE gel under non-reducing condition and western blotted with anti-His tag antibody (FIG. 7B, bottom panel). FIG. 7B shows isoforms of different sMD-2 mutants on non-reduced PAGE. Soluble mutants 38-42, 46-50 and 125-129 are most similar to the WT MD-2 in their abundance of monomers. These mutants also expressed well on the cell surface. Mutants 75-79, 79-83, 106-110 and 116-120 did not express well on the cell surface. The soluble forms of these mutants showed very little monomer.

These data demonstrate that monomer formation correlates with membrane MD-2 surface expression. The exception to this can be found in mutant 127-131, which didn't express on the cell surface but was expressed as a monomer. Therefore this mutant may have lost the ability to associate with TLR4.

Figure 8A:
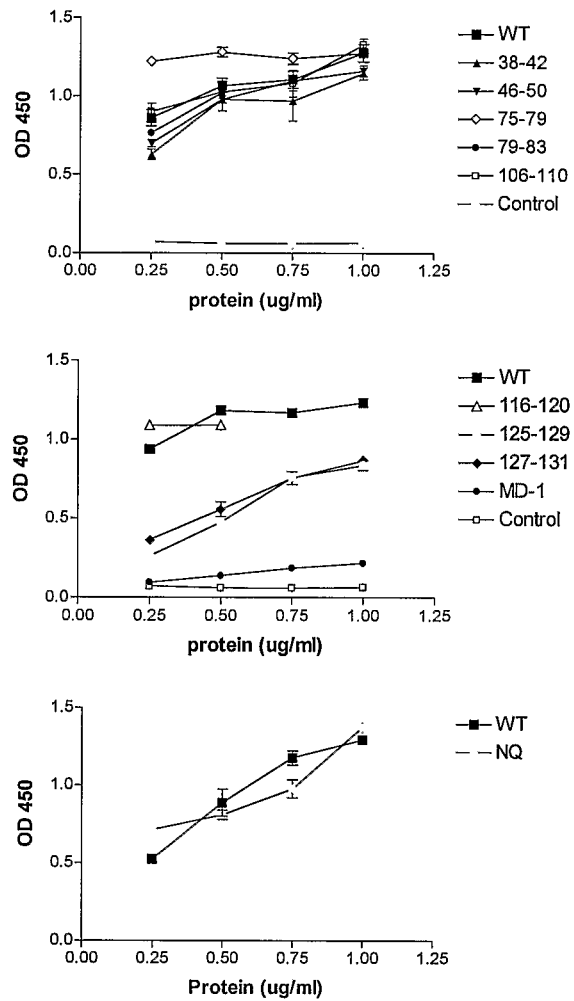
FIGS. 8A and 8B illustrate sMD-2 mutant interaction to lipopolysaccharide (LPS), as described in detail in Example 1, below.
Figure 8B:
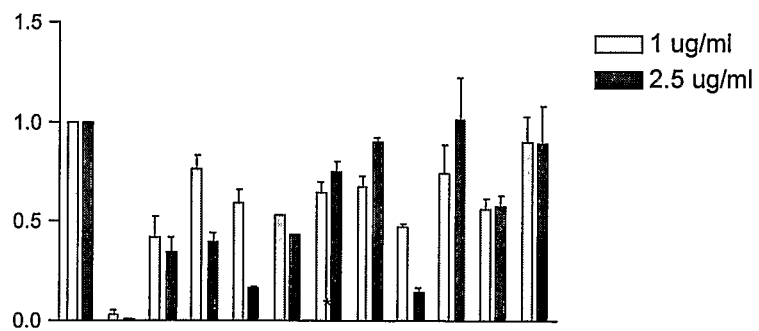

FIG. 8A illustrates sMD-2 mutant interaction to LPS. ELISA assay for sMD-2 binding to LPS coated plate. The plate was coated with LPS and increasing concentrations of sMD-2 WT, sMD-2 mutants, sMD-1 or control His-tag protein were added to the plate. The protein binding to the plate was detected using biotinylated anti His-tag antibody. FIG. 8B illustrates the effect of sMD-2 mutants on CD14 dependent LPS activation in U373 cells. U373 cells were activated with 10 ng/ml LPS and 1 μg/ml CD14. Inhibition of the response with 1 and 2.5 ug/ml of MD-2 or MD-1 were shown as fold difference of IL-6 response from cells in the absence of the added MD-2 or MD-1.

Analysis of Soluble MD-2 Mutant Function

Soluble MD-2 was tested for binding to LPS by using LPS coated plate as described previously. FIG. 8 shows that soluble mutants 38-42, 46-50, 75-79 bound LPS similarly to the wild type. Mutant 79-83 bound more to LPS than the wild type. The unglycosylated mutant bound LPS as well as the wild type. Two mutants, 125-129 and 127-131 bound LPS but less well than the wild type. Our control his-tag protein showed no binding to LPS and MD-1 bound very little LPS.

Previously we have shown that an excess of soluble MD-2 inhibited soluble CD14-dependent LPS activation in the human epithelial cell line U373 perhaps by sequestering LPS. We tested soluble MD-2 mutants for the ability to inhibit LPS activation in this assay. FIG. 9 shows that WT soluble MD-2 at 50 nM efficiently inhibits IL-6 secretion from U373 cells activated with 20 nM soluble CD14 and 100 ng/ml LPS. Mutant 106-110, 116-120, 127-131 and MD-1 fail to sequester LPS. This is in agreement with the LPS coated plate assays showing the defect in LPS binding of these mutants. The rest of the mutants inhibited IL-6 secretion to the various degrees. Although the direct LPS binding assays showed that some of these mutants bind LPS similar to the wild type, none was as efficient as the WT in the U373 inhibition assay.

FIGS. 9A and 9B illustrates sMD-2 mutant binding to TLR4. Flow cytometry analysis of TLR4 transfected CHO cells after incubation with 1 or 5 μg/ml sMD-2 for 15 min or 16 hr. and stained with anti-His tag. The data were presented as fold differences in MCN of fluorescence as compared to the staining of the WT protein.

Figure 10:
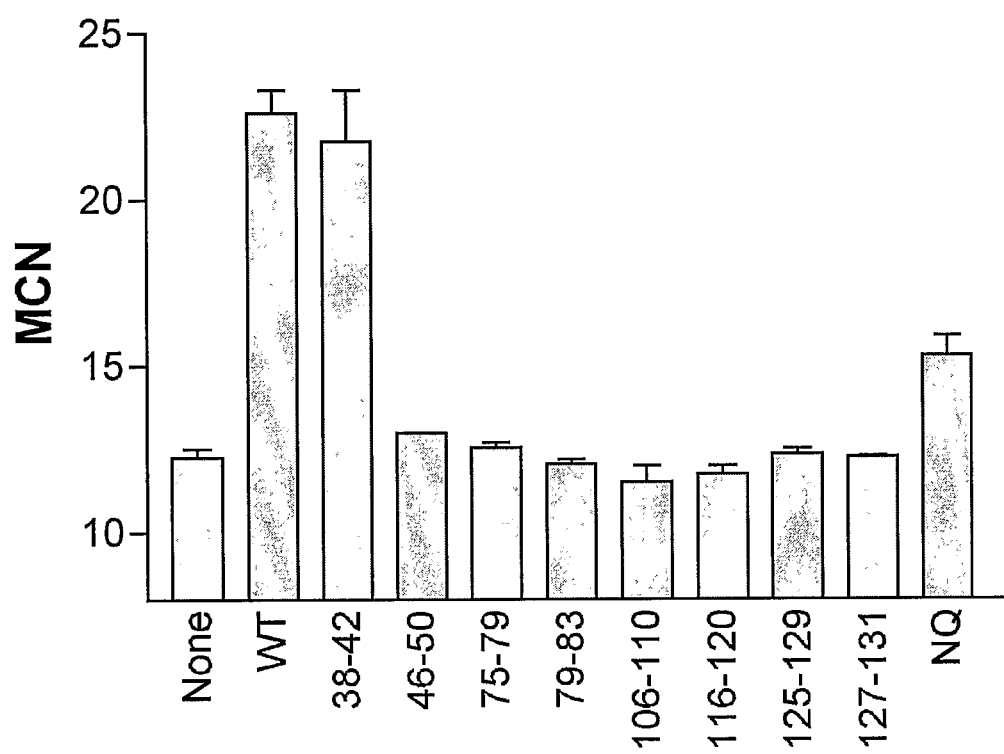
FIG. 10 illustrates data showing LPS activation of sMD-2, as described in detail in Example 1, below.

To determine sMD-2 mutants binding to TLR4, the purified proteins were added to TLR4 transfected EL1 cells, washed off excess protein after 15 min or overnight incubation, stained with anti-His tag antibody and analyzed by FACS. FIG. 10 illustrates data showing LPS activation of sMD-2. TLR4 transfected CHO cells harboring CD25 reporter plasmids were activated with 100 ng/ml LPS in the absence and presence of 5 ug/ml of sMD-2 and the NF-κB activation was measured by FACS analysis of CD25 surface expression (MCN) using anti-CD25-PE. FIG. 10 shows that only mutant 125-129 binds to TLR4 as well as wild type soluble MD-2 while the rest of the mutants bind less than the wild type. Among mutants with monomers, mutants 46-50 and 127-131 did not bind to TLR4 suggesting these are the areas of soluble monomeric MD-2 binding to TLR4. Although we showed that monomer has the highest affinity to TLR4 (FIG. 6), there was no correlation between the amount of monomer and the amount of MD-2 on TLR4 transfected cells after 15 min incubation. When the cells were left for 16 hr before FACS analysis, we observed binding only on the wild type, mutant 38-42 and 125-129. None of mutants with mostly oligomers remained in association to TLR4 cells after 16 hr. The unglycosylated MD-2 bound normally to TLR4 cells after 15 min but the binding was reduced after 16 hr. These data confirm the functional importance of monomeric soluble MD-2. Monomeric MD-2 either binds TLR4 with higher affinity or is more stable in solution than the oligomers.

LPS responsiveness was analyzed by adding soluble MD-2 mutants with 100 ng/ml LPS to TLR4 transfected EL1 cells and assaying for NF-κB dependent CD25 expression by PACS. We found that mutant 38-42 and the unglycosylated mutant that bind tightly to TLR4 can confer LPS responsiveness. Both mutants also bind LPS well. Other mutants which bind well to LPS but fail to associate tightly to TLR4 cells were unable to confer LPS responsiveness. These data show that although both TLR4 and LPS binding are important for soluble MD-2 function. The affinity of soluble MD-2 for TLR4 appears to be more critical for LPS activation than the LPS binding affinity. Mutant 125-129 binds to TLR4 cells tightly but was not able to confer LPS responsiveness. This mutant is defective in LPS binding suggesting that residues 125-129 are critical for LPS binding but not TLR4 binding. Mutant 127-131 is defective in both LPS and TLR4 binding and therefore was unable to confer LPS responsiveness. Mutant 125-129 has alanine replacements in amino acid KFSKG which overlap SKGKY in mutant 127-131. Both mutants are defective in LPS binding but only mutant SKGKY lost TLR4 binding capacity. These data suggest that residues 128-129 (KY) which are critical for TLR4 binding, are adjacent to LPS binding region of sMD-2. Our data agree with previously reports that the hydrophilic basic residues 125-131 as well as the hydrophobic region 116-120 of sMD-2 is important in LPS binding. We set out to explain the behavior of membrane MD-2 by analyzing soluble MD-2 for it's function in TLR4 and LPS binding. It was found that the biological activity of soluble MD-2 mutants to is very different than membrane MD-2 mutants. None of soluble MD-2 mutants is as active as the WT while some membrane MD-2 mutants were overactive.

Discussion

These studies demonstrated that the MD-2 level on the surface of cells expressing TLR4 influences the level of LPS activation. MD-2 is absolutely required for LPS activation. Since MD-2 is present in a relatively small amount as compared to CD14 or LBP, small changes in MD-2 levels are likely to have large effects on cellular activation by LPS. Our observation has implications for the analysis of MD-2 function. We showed in these studies that unglycosylated MD-2 functions normally as a cell surface receptor when expressed at equal levels to the WT. Our results differ from previous studies of da Silva Correia (2002) J. Biol. Chem 277:1845; Ohnishi (2001) J. Immuno. 167:3354, which showed that glycosylation impaired MD-2 function by assaying transiently transfected cell lines with luciferase reporter assay. A limitation of these experiments is that assessment of protein expression and the level of cell activation could not be performed on the same cell population. Due to the highly sensitive nature of the luciferase reporter assay, the amount of TLR4 and MD-2 expression on cell surface could be limited. The analysis of MD-2 levels relied on immunoprecipitation and Western blotting which are less quantitative than FACS.

Analysis of the alanine replacement mutation of membrane MD-2 in stably transfected cell lines showed that the N-terminal 61 amino acid of human MD-2 is not involved in cell surface expression. Nearly all of the rest of MD-2 is involved in surface expression except for three areas. It is interesting that we found certain mutants over-responsive to LPS as compared to the level of expression. Our data agree with previous reports both in mouse and human MD-2, Visintin (2003) J. Biol. Chem. 278:48313; Kawasaki (2003) J. Immunol. 170:413; Re (2003) J. Immunol. 171:5272; that the basic residues 121-129 are not important for surface expression but critical for LPS responsiveness. The soluble MD-2 mutant 125-129 bound to TLR4 cells normally but bound poorly to LPS. It is possible that this property extends to membrane MD-2 which suggests that this region on membrane MD-2 is important for LPS binding. However, since we have no data on direct LPS binding to cells, this conclusion is speculative. The critical regions on human membrane CD14 for LBP-dependent LPS activation were mapped to the N-terminal region with three acidic residue regions and one hydrophobic region by Viriyakosol (1995) J. Biol. Chem. 270:361. It is possible that membrane MD-2 and CD14 bind to different part of LPS.

In addition, the mutant in hydrophobic residues 79-83 also expressed on the cell surface but was LPS unresponsive. The purified protein of this mutant contained little monomer and failed to bind TLR4 transfected cells. It is possible that, although oligomers have poorer capability for binding to TLR4 cells than the monomer, they are stabilized on the cells surface through interaction with other proteins when co-expressed with TLR4. On the other hand, through the intracellular chaperoning of certain proteins (one good candidate for this interaction could be with the heat shock protein gp96 which was shown to interact with TLR4 in the endoplasmic reticulum, see Randow (2001) Nat. Cell. Biol. 3:891), monomer formation may be allowed or alteration of the mutation can be compensated for as proposed by Mullen, et al. (2003) Proc. Natl. Acad. Sci. USA 100:3919.

It was described previously that LPS interaction with cell surface TLR4/MD-2 is distinct from that with soluble MD-2, see Akashi (2003) J. Exp. Med. 198:1035. Interaction of LPS with membrane TLR4/MD-2 requires CD14 (da Silva Correia (2001) J. Biol. Chem. 276:21129) whereas CD14 is not required for soluble MD-2 binding to LPS (Viriyakosol (2001) 276:38044; Gioannini (2004) Proc. Natl. Acad. Sci. USA 101:4186). This is similar to the differences in membrane and soluble CD14 interaction with LPS with respect to the requirement for LBP. A body of evidence points to structural differences of MD-2 bound to TLR4 and soluble MD-2. The mAb, MTS510, which immunoprecipitated TLR4/MD-2 complex failed to bind MD-2 alone, Akashi (2000) J. Immunol. 164:3471. We produced a number of monoclonal antibodies which recognize monomeric soluble MD-2 that failed to recognize TLR4/MD-2 on the cell surface.

Our studies of soluble MD-2 function showed that, unlike membrane MD-2, the requirement for functional MD-2 is very stringent. We found that substitution in amino acids, while leaving the cysteine residues intact, produced a soluble mutant with very little monomer. This suggests that not only cysteines, but a larger region of the protein, play important roles in the changing the oligomeric state of soluble MD-2. It is possible that the mutation changes the surface exposure of the cysteine residues important in interchain disulfide bonding leading to increased oligomerization. Regardless of the amount of monomeric form present, only one alanine substitution mutant of soluble MD-2 was LPS responsive. Even though mutant 38-42 and the unglycosylated mutant were LPS responsive, they were less active than the membrane forms as compared to the WT. The LPS responsiveness correlates with the ability of soluble MD-2 to form stable complexes with TLR4 on the cell surface. While we observed that many soluble MD-2 mutants bound to TLR4 cells after 15 min incubation, the binding was lost if the cells were incubated for 16 hr.

In this study, our purified soluble MD-2 WT had the greatest abundance of monomer which we found to be the most active form for TLR4 binding confirming a previous report, see Re (2002) J. Biol. Chem. 277:23427. Recently it was also shown that the complex of LPS and MD2 monomer was the most active ligand for cellular activation, Gioannini (2004) Proc. Natl. Acad. Sci. USA 101:4186. Soluble MD-2 produced by transiently transfected HEK293T cells contained very little monomeric MD-2 (Mullen (2003) Proc. Natl. Acad. Sci. USA 100:3919) yet the protein was active. It is possible that cell lines are different in stabilizing the TLR4/MD-2 complex on the cell surface. We showed here that a large excess of MD-2 can be present on the surface of TLR4 expressing cells and the amount of MD-2 controls the level of LPS responsiveness. Visintin (2003) J. Biol. Chem. elegantly demonstrated that TLR4 clustering initiates signal transduction by LPS. The significance of oligomer formation in soluble MD-2 and membrane MD-2 in regulation of LPS responsiveness remains to be established.

A number of embodiments of the invention have been described. Nevertheless, it will be understood that various modifications may be made without departing from the spirit and scope of the invention. Accordingly, other embodiments are within the scope of the following claims.

```

What is claimed is:

1. An isolated, recombinant or synthetic polypeptide comprising a polypeptide comprising SEQ ID NO:9, wherein the polypeptide specifically binds a lipopolysaccharide (LPS) but cannot bind or has decreased binding affinity to a toll-like receptor-4 (TLR4).

2. A chimeric protein comprising (i) a first domain comprising or consisting of a polypeptide of claim 1, and (ii) at least a second domain.

3. A pharmaceutical composition comprising the isolated, recombinant or synthetic polypeptide as set forth in claim 1, and a pharmaceutically acceptable excipient.

4. A parenteral formulation comprising the isolated, recombinant or synthetic polypeptide as set forth in claim 1.

5. An enteral formulation comprising the isolated, recombinant or synthetic polypeptide as set forth in claim 1.

6. The chimeric protein of claim 2, wherein the second domain comprises an opsinizing agent.

7. The chimeric protein of claim 6, wherein the opsinizing agent comprises an antibody Fc domain or an antibody that binds to an Fc receptor.

8. The chimeric protein of claim 2, wherein the chimeric protein comprises two or more antibody Fc domains.

9. The chimeric protein of claim 2, wherein the chimeric protein comprises two or more polypeptides of claim 1.

10. The chimeric protein of claim 2, wherein the opsinizing agent comprises a human opsinizing agent.

11. The chimeric protein of claim 2, wherein the chimeric protein is glycosylated.

12. The chimeric protein of claim 2, wherein:

(i) the polypeptide of claim 1 is dimeric;

(ii) the second domain comprises an Fc domain;

(iii) the second domain comprises a protein C, an antibacterial or bacteriostatic peptide or protein, an antibiotic, a cytokine, an immunoregulatory agent, an anti-inflammatory agent, a complement activating agent, a carbohydrate-binding domain or a combination thereof;

(iv) the chimeric protein of (iii) the protein C is a human activated protein C; or (v) the chimeric protein of (iii), wherein the complement activating agent comprises a collagen-like domain, a fibrinogen-like domain or a ficolin.

13. The isolated, recombinant or synthetic polypeptide of claim 1, consisting of SEQ ID NO:9.

14. The chimeric protein of claim 2, wherein the chimeric protein comprises a recombinant fusion protein, or the chimeric protein is a recombinant protein.

15. The chimeric protein of claim 2, wherein the chimeric protein comprises a peptidomimetic or synthetic protein.

16. The isolated, recombinant or synthetic polypeptide of claim 1, wherein the polypeptide is a recombinant protein.

17. The isolated, recombinant or synthetic polypeptide of claim 1, wherein the polypeptide is a peptidomimetic or a synthetic protein.

18. The chimeric protein of claim 2, wherein the first domain is joined to the second domain by a chemical linking agent.

19. A pharmaceutical composition comprising the chimeric protein as set forth in claim 2, and a pharmaceutically acceptable excipient.

20. A parenteral formulation comprising the chimeric protein as set forth in claim 2.

21. An enteral formulation comprising the chimeric protein as set forth in claim 2.

22. The chimeric protein of claim 2, wherein the first domain is joined to the second domain by a chemical linking agent.

* * * * *

SEQUENCE LISTING

<160> NUMBER OF SEQ ID NOS: 40

<210> SEQ ID NO 1
<211> LENGTH: 160
<212> TYPE: PRT
<213> ORGANISM: Homo sapiens
<220> FEATURE:
<223> OTHER INFORMATION: Human MD-2

<400> SEQUENCE: 1

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 2
<211> LENGTH: 624
<212> TYPE: DNA
<213> ORGANISM: Homo sapiens
<220> FEATURE:
<223> OTHER INFORMATION: Human MD-2

<400> SEQUENCE: 2
ggcgggccgc tcccacttcg gcacgagggg cacgaggtaa atcttttctg cttactgaaa      60
aggaagagtc tgatgattag ttactgatcc tctttgcatt tgtaaagctt tggagatatt     120
gaatcatgtt accatttctg ttttttttcca ccctgttttc ttccatattt actgaagctc    180
agaagcagta ttgggtctgc aactcatccg atgcaagtat ttcatacacc tactgtgata    240
aaatgcaata cccaattcca attaatgtta accctgtat  agaattgaaa ggatccaaag    300
```

-continued

```
gattattgca catttctac attccaagga gagatttaaa gcaattatat ttcaatctct    360
atataactgt caacaccatg aatcttccaa agcgcaaaga agttatttgc cgaggatctg    420
atgacgatta ctcttttgc agagctctga agggagagac tgtgaataca acaatatcat    480
tctccttcaa gggaataaaa ttttctaagg gaaaatacaa atgtgttgtt gaagctattt    540
ctgggagccc agaagaaatg ctcttttgct tggagtttgt catcctacac caacctaatt    600
caaattagaa taaattgagt attt                                          624
```

```
<210> SEQ ID NO 3
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 3

Glu Ala Gln Lys Gln Tyr Trp Val Cys Ala Ala Ala Ala Ser Ile
  1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140
```

```
<210> SEQ ID NO 4
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 4

Glu Ala Gln Lys Gln Tyr Trp Val Cys Asn Ser Ser Asp Ala Ser Ala
  1               5                  10                  15

Ala Ala Ala Ala Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
```

```
            100                 105                 110
Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
        130                 135                 140
```

<210> SEQ ID NO 5
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 5

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Ala Ala Ala Ala Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
        130                 135                 140
```

<210> SEQ ID NO 6
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 6

```
Glu Ala Ala Ala Ala Ala Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125
```

```
Met Leu Phe Cys Leu Glu Phe Val Ile Leu His Gln Pro Asn Ser Asn
    130                 135                 140

<210> SEQ ID NO 7
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 7

Glu Ala Gln Lys Gln Tyr Trp Val Cys Asn Ser Ser Ala Ala Ala Ala
  1               5                  10                  15

Ala Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
 50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ile Ser Gly Ser Pro Glu Glu
         115                 120                 125

Met Leu Phe Cys Leu Glu Phe Val Ile Leu His Gln Pro Asn Ser Asn
    130                 135                 140

<210> SEQ ID NO 8
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 8

Glu Ala Gln Lys Gln Tyr Trp Val Cys Asn Ser Ser Asp Ala Ser Ile
  1               5                  10                  15

Ser Tyr Thr Tyr Cys Ala Ala Ala Ala Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
 50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ile Ser Gly Ser Pro Glu Glu
         115                 120                 125

Met Leu Phe Cys Leu Glu Phe Val Ile Leu His Gln Pro Asn Ser Asn
    130                 135                 140

<210> SEQ ID NO 9
```

```
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 9

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ala Ala Ala
            20                  25                  30

Ala Ala Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140

<210> SEQ ID NO 10
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 10

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Ala Ala Ala Ala Ala Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140

<210> SEQ ID NO 11
<211> LENGTH: 144
<212> TYPE: PRT
<213> ORGANISM: Artificial Sequence
<220> FEATURE:
<223> OTHER INFORMATION: Human MD-2 mutant
```

<400> SEQUENCE: 11

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ala Ala Ala His Ile Phe
        35                  40                  45

Tyr Ile Pro Arg Arg Asp Leu Lys Gln Leu Tyr Phe Asn Leu Tyr Ile
        50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
            115                 120                 125

Met Leu Phe Cys Leu Glu Phe Val Ile Leu His Gln Pro Asn Ser Asn
        130                 135                 140

<210> SEQ ID NO 12
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 12

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ala Ala Ala Ala Leu Lys Gln Leu Tyr Phe Asn Leu Tyr Ile
        50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
            115                 120                 125

Met Leu Phe Cys Leu Glu Phe Val Ile Leu His Gln Pro Asn Ser Asn
        130                 135                 140

<210> SEQ ID NO 13
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 13

Glu Ala Gln Lys Gln Tyr Trp Val Cys Asn Ser Ser Asp Ala Ser Ile
1               5                   10                  15

```
Ser Tyr Thr Tyr Cys Asp Lys Met Gln Tyr Pro Ile Ser Ile Asn Val
         20                  25                  30

Asn Pro Cys Ile Glu Leu Lys Gly Ser Lys Gly Leu Leu His Ile Phe
         35                  40                  45

Tyr Ile Pro Arg Arg Asp Leu Ala Ala Ala Ala Asn Leu Tyr Ile
 50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                     85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ile Ser Gly Ser Pro Glu Glu
         115                 120                 125

Met Leu Phe Cys Leu Glu Phe Val Ile Leu His Gln Pro Asn Ser Asn
130                 135                 140
```

<210> SEQ ID NO 14
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 14

```
Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
         20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
 50                  55                  60

Thr Val Ala Ala Ala Ala Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                     85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ile Ser Gly Ser Pro Glu Glu
         115                 120                 125

Met Leu Phe Cys Leu Glu Phe Val Ile Leu His Gln Pro Asn Ser Asn
130                 135                 140
```

<210> SEQ ID NO 15
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 15

```
Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
         20                  25                  30

Asn Pro Cys Ile Glu Leu Lys Gly Ser Lys Gly Leu Leu His Ile Phe
```

-continued

```
                35                  40                  45
Tyr Ile Pro Arg Arg Asp Leu Lys Gln Leu Tyr Phe Asn Leu Tyr Ile
 50                  55                  60

Thr Val Asn Thr Met Asn Leu Pro Lys Ala Ala Ala Ala Cys Arg
 65                  70                  75                  80

Gly Ser Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
                130                 135                 140

<210> SEQ ID NO 16
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 16

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
                 20                  25                  30

Asn Pro Cys Ile Ala Ala Ala Ala Lys Gly Leu Leu His Ile Phe
                 35                  40                  45

Tyr Ile Pro Arg Arg Asp Leu Lys Gln Leu Tyr Phe Asn Leu Tyr Ile
 50                  55                  60

Thr Val Asn Thr Met Asn Leu Pro Lys Arg Lys Glu Val Ile Cys Arg
 65                  70                  75                  80

Gly Ser Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
                130                 135                 140

<210> SEQ ID NO 17
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 17

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
                 20                  25                  30

Asn Pro Cys Ile Glu Leu Lys Gly Ser Lys Gly Leu Leu His Ile Phe
                 35                  40                  45

Tyr Ile Pro Ala Ala Ala Ala Gln Leu Tyr Phe Asn Leu Tyr Ile
 50                  55                  60
```

```
Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
        130                 135                 140
```

<210> SEQ ID NO 18
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 18

```
Glu Ala Gln Lys Gln Tyr Trp Val Cys Asn Ser Ser Asp Ala Ser Ile
  1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Ala Ala
     50                  55                  60

Ala Ala Ala Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
        130                 135                 140
```

<210> SEQ ID NO 19
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 19

```
Glu Ala Gln Lys Gln Tyr Trp Val Cys Asn Ser Ser Asp Ala Ser Ile
  1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Ala Ala Ala Ala Glu Val Ile Cys Arg
 65                  70                  75                  80

Gly Ser Asp Asp Asp Tyr Ser Phe Cys Arg Ala Leu Lys Gly Glu Thr
                 85                  90                  95
```

```
Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
            115                 120                 125

Met Leu Phe Cys Leu Glu Phe Val Ile Leu His Gln Pro Asn Ser Asn
130                 135                 140
```

<210> SEQ ID NO 20
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 20

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
50                  55                  60

Thr Val Asn Thr Met Asn Leu Pro Lys Arg Lys Glu Val Ile Cys Arg
65                  70                  75                  80

Gly Ala Ala Ala Ala Ser Phe Cys Arg Ala Leu Lys Gly Glu Thr
                85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
            115                 120                 125

Met Leu Phe Cys Leu Glu Phe Val Ile Leu His Gln Pro Asn Ser Asn
130                 135                 140
```

<210> SEQ ID NO 21
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 21

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Ala Ala Ala Ala Phe Ser Lys
                100                 105                 110

Gly Lys Tyr Lys Cys Val Val Glu Ala Ile Ser Gly Ser Pro Glu Glu
```

```
            115                 120                 125
Met Leu Phe Cys Leu Glu Phe Val Ile Leu His Gln Pro Asn Ser Asn
    130                 135                 140

<210> SEQ ID NO 22
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 22

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ala Ala Ala Ala Asn Ser Asn
    130                 135                 140

<210> SEQ ID NO 23
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 23

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Ala Ala
                85                  90                  95

Ala Ala Ala Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140
```

```
<210> SEQ ID NO 24
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 24

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ala Ala Ala Ala Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140

<210> SEQ ID NO 25
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 25

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Ala Ala Ala Ala
            100                 105                 110

Ala Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140

<210> SEQ ID NO 26
<211> LENGTH: 144
<212> TYPE: PRT
<213> ORGANISM: Artificial Sequence
```

```
<220> FEATURE:
<223> OTHER INFORMATION: Human MD-2 mutant

<400> SEQUENCE: 26

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ala Ala Ala Ala Pro Glu Glu
         115                 120                 125

Met Leu Phe Cys Leu Glu Phe Val Ile Leu His Gln Pro Asn Ser Asn
     130                 135                 140

<210> SEQ ID NO 27
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 27

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
             20                  25                  30

Asn Pro Cys Ile Glu Leu Lys Gly Ser Lys Gly Leu Leu His Ile Phe
         35                  40                  45

Tyr Ile Pro Arg Arg Asp Leu Lys Gln Leu Tyr Phe Asn Leu Tyr Ile
     50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
             100                 105                 110

Gly Lys Tyr Lys Cys Val Val Glu Ala Ile Ser Gly Ser Pro Ala Ala
         115                 120                 125

Ala Ala Ala Cys Leu Glu Phe Val Ile Leu His Gln Pro Asn Ser Asn
     130                 135                 140

<210> SEQ ID NO 28
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 28
```

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Ala Ala Ala Ala His Gln Pro Asn Ser Asn
    130                 135                 140
```

<210> SEQ ID NO 29
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 29

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Ala Ala Ala Ala Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140
```

<210> SEQ ID NO 30
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 30

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30
```

```
Asn Pro Cys Ile Glu Leu Lys Gly Ser Lys Gly Leu Leu His Ile Phe
            35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Ala Ala Ala Ala Ala Phe Lys Gly Ile Lys Phe Ser Lys
                100                 105                 110

Gly Lys Tyr Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
                130                 135                 140
```

<210> SEQ ID NO 31
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 31

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
            35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ala Ala
                100                 105                 110

Ala Ala Ala Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
                130                 135                 140
```

<210> SEQ ID NO 32
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 32

```
Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
            35                  40                  45

Tyr Ile Pro Arg Arg Asp Leu Lys Gln Leu Tyr Phe Asn Leu Tyr Ile
```

```
            50                  55                  60
Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                    100                 105                 110

Gly Lys Tyr Lys Cys Ala Ala Ala Ala Ser Gly Ser Pro Glu Glu
            115                 120                 125

Met Leu Phe Cys Leu Glu Phe Val Ile Leu His Gln Pro Asn Ser Asn
    130                 135                 140
```

<210> SEQ ID NO 33
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 33

```
Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
                20                  25                  30

Asn Pro Cys Ile Glu Leu Lys Gly Ser Lys Gly Leu Leu His Ile Phe
            35                  40                  45

Tyr Ile Pro Arg Arg Asp Leu Lys Gln Leu Tyr Phe Asn Leu Tyr Ile
        50                  55                  60

Thr Val Asn Thr Met Asn Leu Pro Lys Arg Lys Glu Val Ile Cys Arg
 65                  70                  75                  80

Gly Ser Asp Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                    100                 105                 110

Gly Lys Tyr Lys Cys Val Val Glu Ala Ile Ser Ala Ala Ala Ala
            115                 120                 125

Met Leu Phe Cys Leu Glu Phe Val Ile Leu His Gln Pro Asn Ser Asn
    130                 135                 140
```

<210> SEQ ID NO 34
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 34

```
Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
                20                  25                  30

Asn Pro Cys Ile Glu Leu Lys Gly Ser Lys Gly Leu Leu His Ile Phe
            35                  40                  45

Tyr Ile Pro Arg Arg Asp Leu Lys Gln Leu Tyr Phe Asn Leu Tyr Ile
        50                  55                  60

Thr Val Asn Thr Met Asn Leu Pro Lys Arg Lys Glu Val Ile Cys Arg
 65                  70                  75                  80
```

Gly Ser Asp Asp Tyr Ser Phe Cys Arg Ala Leu Lys Gly Glu Thr
            85                  90                  95

Val Asn Thr Thr Ile Ser Phe Ser Phe Lys Gly Ile Lys Phe Ser Lys
        100                 105                 110

Gly Lys Tyr Lys Cys Val Val Glu Ala Ile Ser Gly Ser Pro Glu Glu
            115                 120                 125

Met Ala Ala Ala Ala Phe Val Ile Leu His Gln Pro Asn Ser Asn
        130                 135                 140

<210> SEQ ID NO 35
<211> LENGTH: 144
<212> TYPE: PRT
<213> ORGANISM: Artificial Sequence
<220> FEATURE:
<223> OTHER INFORMATION: Human MD-2 mutant

<400> SEQUENCE: 35

Glu Ala Gln Lys Gln Tyr Trp Val Cys Asn Ser Ser Asp Ala Ser Ile
1               5                   10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Tyr Ser Phe Cys Arg Ala Leu Lys Gly Glu Thr
            85                  90                  95

Val Asn Thr Thr Ile Ser Phe Ser Phe Lys Gly Ile Lys Phe Ser Lys
        100                 105                 110

Gly Lys Tyr Lys Cys Val Val Glu Ala Ile Ser Gly Ser Pro Glu Glu
            115                 120                 125

Met Leu Phe Cys Leu Glu Phe Val Ile Leu His Ala Ala Ala Ala Ala
        130                 135                 140

<210> SEQ ID NO 36
<211> LENGTH: 16
<212> TYPE: PRT
<213> ORGANISM: Artificial Sequence
<220> FEATURE:
<223> OTHER INFORMATION: Human MD-2 signal peptide

<400> SEQUENCE: 36

Met Leu Pro Phe Leu Phe Phe Ser Thr Leu Phe Ser Ser Ile Phe Thr
1               5                   10                  15

<210> SEQ ID NO 37
<211> LENGTH: 144
<212> TYPE: PRT
<213> ORGANISM: Artificial Sequence
<220> FEATURE:
<223> OTHER INFORMATION: polyA therapeutic human MD-2 variant

<400> SEQUENCE: 37

Glu Ala Gln Lys Gln Tyr Trp Val Cys Asn Ser Ser Asp Ala Ser Ile
1               5                   10                  15

Ser Tyr Thr Tyr Cys Asp Lys Met Gln Ala Ala Ala Ala Ala Asn Val
            20                  25                  30

Asn Pro Cys Ile Glu Leu Lys Gly Ser Lys Gly Leu Leu His Ile Phe

```
              35                  40                  45
Tyr Ile Pro Arg Arg Asp Leu Lys Gln Leu Tyr Phe Asn Leu Tyr Ile
 50                  55                  60

Thr Val Asn Thr Met Asn Leu Pro Lys Arg Lys Glu Val Ile Cys Arg
 65                  70                  75                  80

Gly Ser Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
            130                 135                 140

<210> SEQ ID NO 38
<211> LENGTH: 144
<212> TYPE: PRT
<213> ORGANISM: Artificial Sequence
<220> FEATURE:
<223> OTHER INFORMATION: polyA therapeutic human MD-2 variant

<400> SEQUENCE: 38

Glu Ala Gln Lys Gln Tyr Trp Val Cys Asn Ser Ser Asp Ala Ser Ile
  1               5                  10                  15

Ser Tyr Thr Tyr Cys Asp Lys Met Gln Tyr Pro Ile Ser Ile Asn Val
                 20                  25                  30

Asn Pro Cys Ile Glu Leu Lys Gly Ser Lys Gly Leu Leu His Ile Phe
             35                  40                  45

Tyr Ile Pro Arg Arg Asp Leu Lys Gln Leu Tyr Phe Asn Leu Ala Ala
 50                  55                  60

Ala Ala Ala Thr Met Asn Leu Pro Lys Arg Lys Glu Val Ile Cys Arg
 65                  70                  75                  80

Gly Ser Asp Asp Tyr Ser Phe Cys Arg Ala Leu Lys Gly Glu Thr
                 85                  90                  95

Val Asn Thr Thr Ile Ser Phe Ser Phe Lys Gly Ile Lys Phe Ser Lys
                100                 105                 110

Gly Lys Tyr Lys Cys Val Val Glu Ala Ile Ser Gly Ser Pro Glu Glu
                115                 120                 125

Met Leu Phe Cys Leu Glu Phe Val Ile Leu His Gln Pro Asn Ser Asn
            130                 135                 140

<210> SEQ ID NO 39
<211> LENGTH: 144
<212> TYPE: PRT
<213> ORGANISM: Artificial Sequence
<220> FEATURE:
<223> OTHER INFORMATION: polyA therapeutic human MD-2 variant

<400> SEQUENCE: 39

Glu Ala Gln Lys Gln Tyr Trp Val Cys Asn Ser Ser Asp Ala Ser Ile
  1               5                  10                  15

Ser Tyr Thr Tyr Cys Asp Lys Met Gln Tyr Pro Ile Ser Ile Asn Val
                 20                  25                  30

Asn Pro Cys Ile Glu Leu Lys Gly Ser Lys Gly Leu Leu His Ile Phe
             35                  40                  45

Tyr Ile Pro Arg Arg Asp Leu Lys Gln Leu Tyr Phe Asn Leu Tyr Ile
 50                  55                  60
```

-continued

```
Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Ala Ala Ala Ala
            100                 105                 110

Ala Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140

<210> SEQ ID NO 40
<211> LENGTH: 144
<212> TYPE: PRT
<213> ORGANISM: Artificial Sequence
<220> FEATURE:
<223> OTHER INFORMATION: human MD-2 mature protein

<400> SEQUENCE: 40

Glu Ala Gln Lys Gln Tyr Trp Val Cys Asn Ser Ser Asp Ala Ser Ile
 1               5                  10                  15

Ser Tyr Thr Tyr Cys Asp Lys Met Gln Tyr Pro Ile Ser Ile Asn Val
            20                  25                  30

Asn Pro Cys Ile Glu Leu Lys Gly Ser Lys Gly Leu Leu His Ile Phe
        35                  40                  45

Tyr Ile Pro Arg Arg Asp Leu Lys Gln Leu Tyr Phe Asn Leu Tyr Ile
    50                  55                  60

Thr Val Asn Thr Met Asn Leu Pro Lys Arg Lys Glu Val Ile Cys Arg
65                  70                  75                  80

Gly Ser Asp Asp Asp Tyr Ser Phe Cys Arg Ala Leu Lys Gly Glu Thr
                85                  90                  95

Val Asn Thr Thr Ile Ser Phe Ser Phe Lys Gly Ile Lys Phe Ser Lys
            100                 105                 110

Gly Lys Tyr Lys Cys Val Val Glu Ala Ile Ser Gly Ser Pro Glu Glu
        115                 120                 125

Met Leu Phe Cys Leu Glu Phe Val Ile Leu His Gln Pro Asn Ser Asn
    130                 135                 140
```